US010172782B2

(12) United States Patent
Comeron et al.

(10) Patent No.: US 10,172,782 B2
(45) Date of Patent: Jan. 8, 2019

(54) COMPOSITIONS AND METHODS FOR TREATING HAIR

(71) Applicant: L'OREAL, Paris (FR)

(72) Inventors: Vanessa Comeron, Roselle Park, NJ (US); Aziza Suleiman, Paterson, NJ (US); Anand Mahadeshwar, Scotch Plains, NJ (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 15/282,952

(22) Filed: Sep. 30, 2016

(65) Prior Publication Data
US 2018/0092830 A1    Apr. 5, 2018

(51) Int. Cl.
| A61Q 5/06 | (2006.01) |
| A61K 8/898 | (2006.01) |
| A61K 8/81 | (2006.01) |
| A61K 8/87 | (2006.01) |
| A61K 8/60 | (2006.01) |
| A61K 8/44 | (2006.01) |

(52) U.S. Cl.
CPC .............. *A61K 8/898* (2013.01); *A61K 8/442* (2013.01); *A61K 8/604* (2013.01); *A61K 8/8141* (2013.01); *A61K 8/87* (2013.01); *A61Q 5/06* (2013.01); *A61K 2800/22* (2013.01); *A61K 2800/48* (2013.01); *A61K 2800/594* (2013.01); *A61K 2800/81* (2013.01)

(58) Field of Classification Search
None
See application file for complete search history.

(56) References Cited

U.S. PATENT DOCUMENTS

| 3,110,695 | A | 11/1963 | Ceresa |
| 3,304,273 | A | 2/1967 | Stamberger |
| 3,383,351 | A | 5/1968 | Stamberger |
| 3,412,054 | A | 11/1968 | Milligan et al. |
| 3,523,095 | A | 8/1970 | Laurito et al. |
| 4,301,601 | A | 11/1981 | Carr |
| 4,874,604 | A | 10/1989 | Sramek |
| 5,902,225 | A | 5/1999 | Monson |
| 5,985,295 | A | 11/1999 | Peffly |
| 6,649,173 | B1 | 11/2003 | Arnaud et al. |
| 6,726,916 | B1 | 4/2004 | Ramin |
| 2004/0253297 | A1 | 12/2004 | Hedges et al. |
| 2004/0258628 | A1 | 12/2004 | Riedel et al. |
| 2006/0078520 | A1 | 4/2006 | Pays et al. |
| 2013/0108557 | A1 | 5/2013 | Abram et al. |
| 2013/0287724 | A1 | 10/2013 | Hoffman et al. |
| 2014/0105945 | A1 | 4/2014 | Bui et al. |
| 2015/0004114 | A1 | 1/2015 | Tan et al. |
| 2015/0004116 | A1 | 1/2015 | Tan et al. |
| 2015/0004119 | A1 | 1/2015 | Tan et al. |
| 2015/0004121 | A1 | 1/2015 | Tan et al. |
| 2015/0150772 | A1* | 6/2015 | Krueger ............... A61K 8/42 132/202 |
| 2016/0030307 | A1 | 2/2016 | Chen et al. |
| 2016/0175206 | A1 | 6/2016 | Tan et al. |
| 2016/0175237 | A1* | 6/2016 | Shin .................. A61K 8/895 424/70.9 |
| 2016/0184195 | A1 | 6/2016 | Tan et al. |

FOREIGN PATENT DOCUMENTS

| DE | 1152536 | | 8/1963 | |
| EP | 0216479 | A1 | 4/1987 | |
| EP | 0847752 | A1 | 6/1998 | |
| EP | 0898958 | A1 | 3/1999 | |
| EP | 0898960 | A1 | 3/1999 | |
| FR | 2812543 | A1 | 2/2002 | |
| GB | 1040452 | A | 8/1966 | |
| WO | 2013/064596 | A1 | 5/2013 | |
| WO | 2014/144076 | A1 | 9/2014 | |
| WO | WO 2014/144076 | * | 9/2014 | ............... A61Q 5/06 |
| WO | 2014/210480 | A1 | 12/2014 | |
| WO | 2016/100885 | A1 | 6/2016 | |
| WO | 2017/165931 | A1 | 10/2017 | |

OTHER PUBLICATIONS

Wacker Silicones, "Belsil ADM 8301 E", 2013, pp. 1-2.*
Clariant, "SilCare Silicone SEA", 2004, pp. 1-2.*
English language Abstract for EP 0898960A1, dated Mar. 3, 1999.
Co-pending U.S. Appl. No. 15/282,812, "Foaming Cosmetic Compositions and Methods for Producing the Same," Inventors: Vanessa Comeron et al., filed Sep. 30, 2016.
Co-pending U.S. Appl. No. 15/282,502, "Compositions and Methods for Treating Hair," Inventors: Vanessa Comeron et al., filed Sep. 30, 2016.
Co-pending U.S. Appl. No. 15/282,480, "Compositions and Methods for Treating Hair," Inventors: Vanessa Comeron et al., filed Sep. 30, 2016.
International Search Report for counterpart Application PCT/US2017/054791, dated Dec. 12, 2017.
Non-Final Office Action for copending U.S. Appl. No. 15/282,502, dated Aug. 21, 2017.
Non-Final Office Action for copending U.S. Appl. No. 15/282,952, dated Oct. 6, 2017.
Non-Final Office Action for copending U.S. Appl. No. 15/282,812, dated Oct. 6, 2017.
Non-Final Office Action for copending U.S. Appl. No. 15/282,480, dated Feb. 5, 2018.

(Continued)

*Primary Examiner* — Brian Gulledge
(74) *Attorney, Agent, or Firm* — The Marbury Law Group, PLLC

(57) ABSTRACT

Disclosed herein are compositions and methods for styling hair comprising at least two latex polymers, wherein at least one latex polymer is a film-forming polymer; at least one aminofunctional silicone; at least one amphoteric surfactant; at least one alkylpolyglucoside; at least one anionic thickening agent; and water; wherein the at least two latex polymers are present in a combined amount ranging from about 0.1% to about 30% by weight, relative to the weight of the composition.

28 Claims, No Drawings

(56) References Cited

OTHER PUBLICATIONS

International Search Report and Written Opinion for counterpart Application PCT/US2017/054364, dated Nov. 29, 2017.
International Search Report and Written Opinion for counterpart Application PCT/US2017/054791, dated Feb. 12, 2018.
http://www.gnpd.com. Mintel—Wave Aid, XP002776284, retrieved from Internet Jul. 2016.
http://www.gnpd.com. Mintel—XXL Body Ultra Strong Thickening Mousse, XP002776283, retrieved from Internet Oct. 2012.
Invitation to Pay Additional Fees for counterpart Application No. PCT/EP2017/054356, dated Jan. 9, 2018.
Final Office Action for copending U.S. Appl. No. 15/282,812, dated Mar. 9, 2018.
Comparatively Speaking: Fatty Alcohols vs. Fatty Acids vs. Esters: retrieved from internet: http://www.cosmeticsandtoiletries.com/research/chemistry/97861099.html. retrieved on Aug. 16, 2017.
Fatty Acids, alcohols and esters: retrieved from Internet: http://thenakedchemist.com/fatty-acids-alcohols-and-esthers/. Retrieved on Aug. 16, 2017.
International Search Report and Written Opinion for counterpart Application PCT/US2017/054356, dated Mar. 15, 2018.
Final Office Action for copending U.S. Appl. No. 15/282,502, dated Apr. 10, 2018.
Non-Final Office Action for copending U.S. Appl. No. 15/282,480, dated Aug. 16, 2018.
Non-Final Office Action for copending U.S. Appl. No. 15/282,812, dated Aug. 28, 2018.

* cited by examiner

COMPOSITIONS AND METHODS FOR TREATING HAIR

FIELD OF THE INVENTION

The disclosure relates to compositions for use on keratinous substances. In particular, it relates to a composition and methods for styling the hair.

BACKGROUND

Compositions for styling the hair are known, such as, for example, hair spray compositions, hair gels and mousses, hair volumizing compositions, hair smoothing creams, lotions, serums, oils, clays, etc. The goals of many hair styling compositions include holding or fixing the hair in a particular shape, imparting or increasing volume of the hair, smoothing the hair, and/or decreasing or eliminating the appearance of frizz.

Drawbacks associated with current products for styling the hair include that the product can be sticky or tacky and/or can produce a film that imparts a sticky or tacky feel. Moreover, hair styled with current products can be stiff and/or "crunchy" in that the film is hard and brittle resulting in a crunching feel or sound when the hair is touched, which is undesirable for most consumers.

Current products for styling the hair typically include water-soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, and often as the concentration of the polymer increases, its viscosity rapidly increases. In styling applications, as the solvent evaporates, the polymer solution becomes thicker on the hair surface, resulting in a sticky or tacky film. These products also tend to exhibit problems with product spreadability, hair manageability, and humidity resistance, which is especially a problem in hot and humid environments.

Particularly, while previous compositions comprising latex polymers may provide clean properties to the hair given its anionic nature, the clean properties can translate into difficult application and/or distribution of the product, quick absorption, dryness, and/or possibly static in the hair. The presence of film formers can also leave the hair with a stiff, crunchy, and/or sticky feel. Often, traditional silicones may be used to overcome the brittleness and stiffness caused by the film, however this tends to make the hair feel greasy and oily. Alternative conditioning agents, such as non-ionic silicones and humectants, can actually plasticize the film produced by the product, thus affecting its high humidity curl retention, and creating build up, which weighs down the hair.

It has now been surprisingly and unexpectedly discovered that combining at least two latex polymers, wherein at least one latex polymer is a film-forming polymer, with at least one aminofunctional silicone, at least one amphoteric surfactant, at least one alkylpolyglucoside, at least one anionic thickening agent, produces a composition that exhibits excellent conditioning properties in wet and dry stages of hair while maintaining desirable care benefits and styling and shaping properties. Such compositions can allow for a clean, natural, and/or "invisible" feel; a lack of stickiness; frizz control; high humidity resistance; curl and/or wave definition; and styling hold with or without the use of heat. Some compositions may be useful in hair-styling applications wherein styling benefits such as natural look, curling or straightening, and/or styling hold are imparted to hair.

SUMMARY

The disclosure relates, in various embodiments, to a cosmetic composition comprising at least two latex polymers, wherein at least one latex polymer is a film-forming polymer; at least one aminofunctional silicone; at least one amphoteric surfactant; at least one alkylpolyglucoside; at least one anionic thickening agent; and water; wherein the at least two latex polymers are present in a combined amount ranging from about 0.1% to about 30% by weight, relative to the weight of the composition.

In various embodiments, the at least two latex polymers in the composition of the present invention are present in a combined amount ranging from about 0.25% to about 20% by weight, or from about 0.3% to about 15% by weight, or from about 0.4% to about 10% by weight, or from about 0.5% to about 5% by weight, relative to the total weight of the composition.

In an embodiment, the at least two latex polymers in the composition of the present invention comprise at least one acrylate latex polymer and at least one polyurethane latex polymer.

In an embodiment, the weight ratio of the at least one acrylate latex polymer to the at least one polyurethane latex polymer is greater than 1.

In an embodiment, the weight ratio of the at least one acrylate latex polymer to the at least one polyurethane latex polymer is greater than 2.

In various embodiments, the weight ratio of the at least one acrylate latex polymer to the at least one polyurethane latex polymer ranges from greater than 1 to about 5 or from about 1.5 to about 3.

In an embodiment, the at least one aminofunctional silicone in the composition of the present invention is present in an amount ranging from about 0.0.05% to about 10% by weight, or from about 0.1% to about 7.5% by weight, or from about 0.2% to about 5% by weight, or from about 0.25% to about 3% by weight, relative to the total weight of the composition.

In an embodiment, the at least one aminofunctional silicone in the composition of the present invention is chosen from amodimethicone/morpholinomethyl silsesquioxane copolymer, amodimethicone, PEG-40/PPG-8 methylaminopropyl/hydroxypropyl dimethicone copolymers, trideceth-9 PG-amodimethicone, or mixtures thereof.

In various embodiments, the at least one amphoteric surfactant in the composition of the present invention is present in an amount ranging from about 0.01% to about 5% by weight, or from about 0.05% to about 4% by weight, or from about 0.06% to about 3% by weight, or relative to the total weight of the composition.

In an embodiment, the at least one amphoteric surfactant in the composition of the present invention is chosen from cocamidopropyl betaine, coco-betaine, cocoamphodiacetate and its salts, or mixtures thereof.

In various embodiments, the at least one alkylpolyglucoside in the composition of the present invention is present in an amount ranging from about 0.01% to about 5% by weight, or from about 0.05% to about 4% by weight, or from about 0.08% to about 3% by weight, relative to the total weight of the composition.

In an embodiment, the at least one alkylpolyglucoside in the composition of the present invention is chosen from decyl glucoside, lauryl glucoside, stearyl glucoside, coco-glucoside, or mixtures thereof.

In an embodiment, the at least one anionic thickening agent in the composition of the present invention is chosen from anionic acrylates copolymers, anionic polyacrylates, or mixtures thereof.

In an embodiment, the at least one anionic thickening agent in the composition of the present invention is chosen from copolymers of (meth)acrylic acid, methylacrylate and dimethyl meta-isopropenyl benzyl isocyanate of ethoxylated alcohols, such as polyacrylate-3.

In various embodiments, the at least one anionic thickening agent in the composition of the present invention is present in an amount ranging from about 0.01% to about 15% by weight, or from about 0.1% to about 10% by weight, or from about 0.2% to about 5% by weight, or from about 0.3% to about 2% by weight, relative to the total weight of the composition.

In an embodiment, the cosmetic composition of the present invention is in the form of a mousse.

In an embodiment, the cosmetic composition of the present invention further comprises at least one propellant and is in the form of a mousse.

In an embodiment, the cosmetic composition of the present invention further comprises an additional thickening agent, present in a total amount ranging from about 0.01% to about 10% by weight, relative to the total weight of the composition.

In an embodiment, the additional thickening agent is chosen from acrylamidopropane-sulfonic acid, polysaccharides, gums, guar gums, celluloses, glucans, silicas or hydrophobic silicas, nonionic homopolymers or copolymers containing ethylenically unsaturated monomers of the amide type, modified or unmodified carboxyvinyl polymers, polyacrylamides, sodium salts of polyhydroxycarboxylic acids, polymers comprising at least one hydrophilic unit and at least one fatty-chain allyl ether unit, or mixtures thereof, present in a total amount ranging from about 0.01% to about 10% by weight, relative to the total weight of the composition. Preferably, the additional thickening agent is chosen from xanthan gum, guar gum, hydroxypropyl guar, guar hydroxypropyl trimonium chloride, hydroxyethyl cellulose, hydroxypropyl cellulose, cetyl hydroxyethyl cellulose, or mixtures thereof.

In an embodiment, the cosmetic composition of the present invention further comprises at least one coalescing agent and/or plasticizer, present in a total amount ranging from about 0.1% to about 20% by weight, relative to the total weight of the composition.

In an embodiment, the cosmetic composition of the present invention further comprises at least one coalescing agent and/or plasticizer chosen from glycol ethers, glycol esters, sucrose esters, propylene glycol ethers, propylene glycol esters, propylene glycol dibenzoate, dipropylene glycol dibenzoate, propylene glycol butyl ether, or mixtures thereof.

In an embodiment, the cosmetic composition of the present invention further comprises at least one organic solvent.

In an embodiment, the cosmetic composition of the present invention further comprises at least one additional component chosen from nonionic surfactants, anionic surfactants, cationic surfactants, organic amines, carbonate compounds, emulsifying agents, fillers, pigments, conditioning agents, moisturizing agents, shine agents, sequestering agents, fragrances, preservatives, pH modifiers/neutralizing agents, stabilizers, salts, or mixtures thereof.

In an embodiment, the cosmetic composition of the present invention comprises:
at least one acrylate latex polymer;
at least one polyurethane latex polymer;
at least one aminofunctional silicone chosen from amodimethicone/morpholinomethyl silsesquioxane copolymer, amodimethicone, PEG-40/PPG-8 methylaminopropyl/hydroxypropyl dimethicone copolymers, trideceth-9 PG-amodimethicone, or mixtures thereof, and preferably chosen from amodimethicone/morpholino ethyl silsesquioxane copolymer, trideceth-9 PG-amodimethicone, or mixtures thereof;
at least one amphoteric surfactant chosen from cocamidopropyl betaine, coco-betaine, cocoamphodiacetate and its salts, or mixtures thereof;
at least one alkylpolyglucoside chosen from decyl glucoside, lauryl glucoside, stearyl glucoside, coco-glucoside, or mixtures thereof;
at least one anionic thickening agent comprising polyacrylate-3; and
water;
wherein the weight ratio of the at least one acrylate latex polymer to the at least one polyurethane latex polymer is greater than 1.

The present invention also relates to a method of styling or shaping hair, the method comprising applying to the hair a composition comprising:
at least two latex polymers, wherein at least one latex polymer is a film-forming polymer;
at least one aminofunctional silicone;
at least one amphoteric surfactant;
at least one alkylpolyglucoside;
at least one anionic thickening agent; and
water.

In an embodiment, the above-described method further comprises a step of treating the hair with heat at a temperature ranging from about 25° C. to about 250° C. before, during, or after the application of said composition.

Additional features and advantages of the disclosed embodiments as claimed will be set forth in the detailed description which follows, and in part will be readily apparent to those skilled in the art from that description or recognized by practicing the invention as claimed herein, including the detailed description which follows, as well as the claims.

It is to be understood that both the foregoing general description and the following detailed description present various embodiments of the disclosure, and are intended to provide an overview or framework for understanding the nature and character of the claims.

Latex Polymers

The compositions according to the disclosed embodiments comprise at least two latex polymers, wherein at least one latex polymer is a film-forming polymer.

In various embodiments, the latex polymers may be identified as polymer A and polymer B. Compositions according to certain embodiments may comprise at least one polymer A and at least one polymer B, wherein at least one of polymer A and polymer B is a film-forming polymer.

According to some embodiments, polymer A may be chosen from latex polymers having a Young's modulus ranging from about 0.1 MPa to about 10 MPa and a strain, under stress at 0.5 MPa, of at least about 1%; and polymer B may be chosen from latex polymers having a Young's modulus ranging from about 10 MPa to about 6 GPa and a strain, under stress at 0.5 MPa, of less than about 5%.

In at least certain embodiments, polymer A may have a glass transition temperature (Tg) ranging from about −90° C. to about 40° C., and polymer B may have a glass transition temperature (Tg) ranging from about 40° C. to about 200° C.

In at least certain other embodiments, the weight ratio of polymer A to polymer B in the compositions of the disclosure is from about 1:10 to about 1:1, or from about 3:1 to about 10:1, or from about 5:1 to about 10:1.

According to some embodiments, polymers A and B may be chosen from acrylate and polyurethane polymers, with the proviso that when polymer A is chosen from an acrylate polymer, polymer B is chosen from a polyurethane polymer; and when polymer A is chosen from a polyurethane polymer, polymer B is chosen from an acrylate polymer.

In some embodiments, latex polymers A and B may be chosen such that polymer A comprises at least one latex polymer which is optionally a film-forming polymer that is a relatively soft, flexible latex polymer, and polymer B comprises at least one latex polymer which is optionally a film-forming polymer that is a relatively hard, brittle polymer At least one of polymer A and polymer B is a film-forming polymer. In various embodiments, latex polymer A is a film-forming polymer and latex polymer B is a non-film-forming polymer. In other embodiments, latex polymer A is a non-film-forming polymer and latex polymer B is a film-forming polymer. In further embodiments, both latex polymer A and latex polymer B are film-forming polymers.

As used herein, a film-forming polymer is meant to include a polymer that is capable, by itself or in the presence of an auxiliary film-forming agent, of forming a macroscopically continuous film that adheres to keratin materials, and preferably a cohesive film, better still, a film whose cohesion and mechanical properties are such that said film can be isolated and manipulated individually, for example, when said film is prepared by pouring onto a non-stick surface such as Teflon-coated or silicone-coated surface. In addition, as used herein, a non-film-forming polymer is meant to include a polymer which will not form a film at or below ambient temperature, or in other words, will only form a film at temperatures above ambient. For purposes of this disclosure, ambient temperature is below about 40° C., such as ranging from about 15° C. to about 30° C.

In various embodiments, the latex polymers are provided in the form of aqueous dispersions prior to formulating the compositions of the disclosure. In other embodiments, the aqueous dispersions may be obtained through an emulsion polymerization of monomers wherein the resulting latex polymers have a particle size less than about 1 μm. In certain other embodiments, a dispersion prepared by the polymerization in water of one or more monomers having a polymerizable double bond may be chosen. In other embodiments, the latex polymers are produced from condensation reactions between monomers and subsequently dispersed in an aqueous medium.

In various embodiments, the latex polymers may exist as dispersed polymer particles in a dispersion medium, such as an aqueous dispersion medium. In other embodiments, the latex polymers may be dispersed in independent dispersion media. In further embodiments, the latex polymers may be dispersed together in the same dispersion medium.

The dispersion medium comprises at least one solvent chosen from water. The dispersion medium may further comprise at least one solvent chosen from cosmetically acceptable organic solvents. Cosmetically acceptable organic solvents may, in various embodiments, be water-miscible, e.g. capable of forming at about 25° C. a homogeneous mixture that is transparent, or substantially transparent, to the eye. For instance, cosmetically acceptable organic solvents may be chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, for example, isododecane and mineral oil; and silicones, for example dimethicones, cyclic dimethicones (INCI name: cyclomethicones), and cyclopentasiloxane; or mixtures thereof.

In other embodiments, the solvent of the dispersion medium comprises water. In other embodiments, the solvent of the dispersion medium comprises water and at least one cosmetically acceptable organic solvent. In further embodiments, the solvent comprises water. In further embodiments, the solvent of the dispersion medium primarily consists essentially of water. For example, the solvent of the dispersion medium may, in at least certain exemplary embodiments, comprise greater than about 50% water, greater than about 55% water, greater than about 60% water, greater than about 65% water, greater than about 70% water, greater than about 75% water, greater than about 80% water, greater than about 85% water, greater than about 90% water, greater than about 95% water, greater than about 96% water, greater than about 97% water, greater than about 98% water, or greater than about 99% water.

In various embodiments, the latex polymer particles are not soluble in the solvent of the dispersion medium, i.e. are not water soluble and/or are not soluble in the at least one cosmetically acceptable organic solvent. Accordingly, the latex polymers retain their particulate form in the solvent or solvents chosen.

In another embodiment, the aqueous dispersions obtained through an emulsion polymerization may be spray-dried.

In certain embodiments, latex particles according to the disclosure may have an average diameter ranging up to about 1000 nm, from about 50 nm to about 800 nm, or from about 100 nm to about 500 nm. Such particle sizes may be measured with a laser granulometer (e.g. Brookhaven BI90).

In various embodiments, the latex polymers may, independently, be neutralized, partially neutralized, or unneutralized. In other embodiments where the latex polymers are neutralized or partially neutralized, the particle size may be, for example, greater than about 800 nm. In certain embodiments, the particulate form of the latex polymers is retained in the dispersion medium.

In various embodiments, the latex polymers may be chosen from uncharged and charged latex polymers. In other embodiments, the latex polymers may be chosen from nonionic latex polymers, cationic latex polymers, and anionic latex polymers.

In some embodiments, the latex polymers may be chosen, independently, from acrylate latex polymers and polyurethane latex polymers. As described herein, it is to be understood that when latex polymer A is chosen from an acrylate polymer, latex polymer B is chosen from a polyurethane polymer; and when latex polymer A is chosen from a polyurethane polymer, latex polymer B is chosen from an acrylate polymer.

In certain embodiments, one of the at least two latex polymers may be chosen from acrylate latex polymers, such as those resulting from the homopolymerization or copolymerization of monomers chosen from (meth)acrylics, (meth)acrylates, (meth)acrylamides and/or vinyl homopolymers or copolymers. The term "(meth)acryl" and variations thereof, as used herein, means acryl or methacryl.

In certain embodiments, the (meth)acrylic monomers may be chosen from acrylic acid, methacrylic acid, citraconic acid, itaconic acid, maleic acid, fumaric acid, crotonic acid, maleic anhydride, or mixtures thereof.

In certain embodiments, the (meth)acrylic monomers may be chosen from C1-C8 alkyl (meth)acrylic, methyl (meth)acrylic, ethyl (meth)acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth)acrylic, cyclohexyl (meth)acrylic, isohexyl (meth)acrylic, heptyl (meth)acrylic, isoheptyl (meth)acrylic, octyl (meth)acrylic, isooctyl (meth)acrylic, or mixtures thereof.

In certain embodiments, the esters of (meth)acrylic monomers may be chosen from C1-C8 alkyl (meth)acrylate, methyl (meth)acrylate, ethyl (meth)acrylate, propyl (meth)acrylate, isopropyl (meth)acrylate, butyl (meth)acrylate, tert-butyl (meth)acrylate, pentyl(meth) acrylate, isopentyl (meth)acrylate, neopentyl (meth)acrylate, hexyl (meth)acrylate, isohexyl (meth)acrylate, 2-ethylhexyl (meth)acrylate, cyclohexyl (meth)acrylate, isohexyl (meth)acrylate, heptyl (meth)acrylate, isoheptyl (meth)acrylate, octyl (meth)acrylate, isooctyl (meth)acrylate, allyl (meth)acrylate, or combinations thereof.

In certain embodiments, the esters of (meth)acrylic monomers may be chosen from C1-C8 alkoxy (meth)acrylate, methoxy (meth)acrylate, ethoxy (meth)acrylate, propyl oxide (meth)acrylate, isopropyl oxide (meth)acrylate, butyl oxide (meth)acrylate, tert-butyl oxide (meth)acrylate, pentyl oxide (meth) acrylate, isopentyl oxide (meth)acrylate, neopentyl oxide (meth)acrylate, C2-C6 hydroxy alkyl (meth)acrylates, hydroxy ethyl (meth)acrylate, 2-hydroxypropyl (meth)acrylate, glycidyl (meth)acrylate, ethylene glycol di(meth)acrylate, polyethylene glycol mono(meth)acrylate, 1,4-butane diol di(meth)acrylate, 1,6,hexane diol di(meth) acrylate, aryl (meth)acrylates benzyl (meth)acrylate, phenyl (meth)acrylate, or mixtures thereof.

In certain embodiments, the esters can further contain amino groups such as aminoethyl (meth)acrylate, N,N-dimethylaminoethyl (meth)acrylate, N,N-dimethylaminopropyl (meth)acrylate, N,N-dimethylaminodimethylpropyl (meth)acrylate, N,N-diethyleaminoethyl (meth)acrylate, N,N,N-trimethylaminoethyl (meth)acrylate, salts of the ethylenic amines, or silicone macromonomers.

In various embodiments, the alkyl group of the esters may be either fluorinated or perfluorinated, for example one, some, or all of the hydrogen atoms of the alkyl group are substituted with fluorine atoms. In other embodiments, the monomers can also be fluorine-containing monomers, such as trifluoroethyl methacrylate, 2,2,3,3,3-tetrafluoropropyl methacrylate, 2,2,3,3,4,4-hexafluorobutyl methacrylate, perfluorooctyl methacrylate, or perfluorooctyl acrylate.

In certain embodiments, the amides of (meth)acrylic monomers can, for example, be made of (meth)acrylamide, N-alkyl (meth)acrylamides, N—(C1-C12) alkyl (meth)acrylates such as N-ethyl (meth)acrylamide, N-t-butyl (meth) acrylamide, N-t-octyl (meth)acrylamide, N-methylol (meth) acrylamide, N-diacetone (meth)acrylamide, or mixtures thereof.

In certain embodiments, the vinyl monomers can include, but are not limited to, vinyl cyanide compounds such as acrylonitrile and methacrylonitrile; vinyl esters such as vinyl formate, vinyl acetate, vinyl propionate, vinyl neodecanoate, vinyl pivalate, vinyl benzoate, vinyl t-butyl benzoate, and triallyl cyanurate; vinyl halides such as vinyl chloride and vinylidene chloride; aromatic mono- or divinyl compounds such as styrene, α-methylstyrene, chlorostyrene, alkylstyrene, divinylbenzene and diallyl phthalate; or mixtures thereof. In other embodiments, the vinyl monomers can include para-styrensulfonic, vinylsulfonic, 2-(meth)acryloyloxyethylsulfonic, or 2-(meth)acrylamido-2-methylpropylsulfonic acids.

The list of monomers given is not limiting, and it should be understood that it is possible to use any monomer known to those skilled in the art which includes acrylic and/or vinyl monomers (including monomers modified with a silicone chain).

In certain embodiments, silicone acrylic polymers may also optionally be used as vinyl polymer in at least one exemplary and non-limiting embodiment.

In certain embodiments, acrylic latex polymers may be chosen from aqueous dispersions of Methacrylic Acid/Ethyl Acrylate copolymer (INCI name: Acrylates Copolymer, such as Luviflex® Soft sold by the company BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI name: Polyacrylate-2 Crosspolymer, such as Fixate™ Superhold sold by the company Lubrizol), Butyl acrylate, PEG-10 acrylate, PPG-6 acrylate and dimethylacrylamide copolymer (INCI name: Polyacrylate-3 crosspolymer), Styrene/Acrylic copolymer (such as Neocryl® A-1120 sold by the company DSM), Ethylhexyl Acrylate/Methyl Methacrylate/Butyl Acrylate/Acrylic Acid/Methacrylic Acid copolymer (INCI name: Acrylates/Ethylhexyl Acrylate Copolymer, such as Daitosol 5000SJ sold by the company Daito Kasei Kogyo), Acrylic/Acrylates Copolymer (INCI name: Acrylates Copolymer, such as Daitosol 5000AD sold by the company Daito Kasei Kogyo), or Acrylic copolymers and Acrylates Copolymers (such as VINYSOL 2140 sold by the company Daido Chemical, Aculyn™ 33 sold by the company Dow Chemical, Luvimer® MAE sold by the company BASF, or Balance® CR sold by the company Akzo Nobel).

In other embodiments, one of the at least two latex polymers may be chosen from polyurethane latex polymers, such as aqueous polyurethane dispersions comprising the reaction products of (i), (ii), and/or (iii), defined below.

Reaction product (i) may be any prepolymer according to the formula:

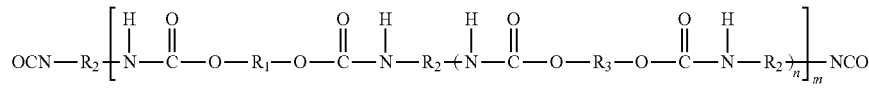

wherein $R_1$ is chosen from bivalent radicals of a dihydroxyl functional compound, $R_2$ is chosen from hydrocarbon radicals of an aliphatic or cycloaliphatic polyisocyanate, $R_3$ is chosen from radicals of a low molecular weight diol, optionally substituted with ionic groups, n ranges from about 0 to about 5, and m is greater than about 1.

Suitable dihydroxyl compounds for providing the bivalent radical $R_1$ include those having at least two hydroxy groups, and having number average molecular weights ranging from about 700 to about 16,000, such as, for example, from about 750 to about 5000. Non-limiting examples of the high molecular weight compounds include polyester polyols, polyether polyols, polyhydroxy polycarbonates, polyhydroxy polyacetals, polyhydroxy polyacrylates, polyhydroxy polyester amides, polyhydroxy polyalkadienes and polyhydroxy polythioethers. In various embodiments, polyester polyols, polyether polyols, or polyhydroxy polycarbonates may be chosen. Mixtures of such compounds are also within the scope of the disclosure.

In some embodiments, the polyester diol may optionally be prepared from aliphatic, cycloaliphatic, or aromatic dicarboxylic or polycarboxylic acids, or anhydrides thereof; and dihydric alcohols such as diols chosen from aliphatic, alicyclic, or aromatic diols.

In other embodiments, the aliphatic dicarboxylic or polycarboxylic acids may be chosen from succinic, fumaric, glutaric, 2,2-dimethylglutaric, adipic, itaconic, pimelic, suberic, azelaic, sebacic, maleic, malonic, 2,2-dimethylmalonic, nonanedicarboxylic, decanedicarboxylic, dodecanedioic, 1,3-cyclohexanedicarboxylic, 1,4-cyclohexanedicarboxylic, 2,5-norboranedicarboxylic, diglycolic, thiodipropionic, 2,5-naphthalenedicarboxylic, 2,6-naphthalenedicarboxylic, phthalic, terephthalic, isophthalic, oxanic, o-phthalic, tetrahydrophthalic, hexahydrophthalic, trimellitic acid, or mixtures thereof.

In various embodiments, the acid anhydrides may be chosen from o-phthalic, trimellitic, succinic acid anhydride or mixtures thereof. In another embodiment, the dicarboxylic acid may be adipic acid.

In certain embodiments, the dihydric alcohols may be chosen from, for example, ethanediol, ethylene glycol, diethylene glycol, triethylene glycol, trimethylene glycol, tetraethylene glycol, 1,2-propanediol, dipropylene glycol, tripropylene glycol, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, cyclohexanedimethanol, 1,8-octanediol, 1,10-decanediol, 1,12-dodecanediol, neopentyl glycol, or mixtures thereof. In other embodiments, the cycloaliphatic and/or aromatic dihydroxyl compounds may also be suitable as the dihydric alcohol(s) for the preparation of the polyester polyol(s).

In certain embodiments, the polyester diols may be chosen from homopolymers or copolymers of lactones, which are, in at least certain embodiments, obtained by addition reactions of lactones or lactone mixtures, such as butyrolactone, ε-caprolactone and/or methyl-ε-caprolactone with the appropriate polyfunctional, for example difunctional, starter molecules such as, for example, the dihydric alcohols mentioned above. In some embodiments, the corresponding polymers of ε-caprolactone may be chosen.

In certain embodiments, the polyester polyol, for example polyester diol, radical $R_1$, may be obtained by polycondensation of dicarboxylic acids, such as adipic acid, with polyols, for example diols, such as hexanediol, neopentyl glycol, or mixtures thereof.

In certain embodiments, the polycarbonates containing hydroxyl groups comprise those known per se, such as the products obtained by reacting diols, such as (1,3)-propanediol, (1,4)-butanediol and/or (1,6)-hexanediol, diethylene glycol, triethylene glycol, or tetraethylene glycol with diaryl carbonates, for example diphenyl carbonate or phosgene.

In certain embodiments, optional polyether polyols may be obtained in any known manner by reacting starting compounds which contain reactive hydrogen atoms with alkylene oxides, such as ethylene oxide; propylene oxide; butylene oxide; styrene oxide; tetrahydrofuran; epichlorohydrin, or mixtures thereof. In certain embodiments, the polyethers do not contain more than about 10% by weight of ethylene oxide units. In other embodiments, polyethers obtained without addition of ethylene oxide may be chosen.

In other embodiments, polyethers modified with vinyl polymers may be chosen. Products of this type can be obtained by polymerization, for example, of styrene and acrylonitrile in the presence of polyethers, for example as described in U.S. Pat. Nos. 3,383,351; 3,304,273; 3,523,095; 3,110,695; and German patent 1 152 536, all incorporated by reference herein.

In certain embodiments, the polythioethers may be chosen from condensation products obtained from thiodiglycol per se and/or with other glycols, dicarboxylic acids, formaldehyde, aminocarboxylic acids, and/or amino alcohols. In other embodiments, the products obtained are either mixed polythioethers, polythioether esters, or polythioether ester amides, depending on the co-components.

In certain embodiments, the polyacetals may be chosen from compounds which can be prepared from aldehydes, such as formaldehyde, and from glycols, such as diethylene glycol, triethylene glycol, ethoxylated 4,4'-(dihydroxy)diphenyl-dimethylmethane, or (1,6)-hexanediol. Polyacetals according to various non-limiting embodiments of the disclosure can also be prepared by polymerization of cyclic acetals.

In certain embodiments, optional polyhydroxy polyesteramides and polyamines include, for example, the mainly linear condensation products obtained from saturated or unsaturated, polybasic carboxylic acids or anhydrides thereof; from saturated or unsaturated, polyvalent amino alcohols; from diamines; from polyamines; or mixtures thereof.

In certain embodiments, optional monomers for the production of polyacrylates having hydroxyl functionality include acrylic acid, methacrylic acid, crotonic acid, maleic anhydride, 2-hydroxyethyl acrylate, 2-hydroxyethyl methacrylate, 2-hydroxypropyl acrylate, 2-hydroxypropyl methacrylate, 3-hydroxypropyl acrylate, 3-hydroxypropyl methacrylate, glycidyl acrylate, glycidyl methacrylate, 2-isocyanatoethyl acrylate, or 2-isocyanatoethyl methacrylate.

In certain embodiments, mixtures of dihydroxy compounds may be chosen.

In various embodiments, optional polyisocyanates for providing the hydrocarbon-based radical $R_2$ include, for example, organic diisocyanates having a molecular weight ranging from about 100 to about 1500, from about 112 to about 1000, or from about 140 to about 400.

In other embodiments, optional diisocyanates are chosen from the general formula $R_2(NCO)_2$, in which $R_2$ represents a divalent aliphatic hydrocarbon group comprising from about 4 to 18 carbon atoms, a divalent cycloaliphatic hydrocarbon group comprising from about 5 to 15 carbon atoms, a divalent araliphatic hydrocarbon group comprising from about 7 to 15 carbon atoms, or a divalent aromatic hydrocarbon group comprising from about 6 to 15 carbon atoms. Examples of the organic diisocyanates include tetramethylene diisocyanate, 1,6-hexamethylene diisocyanate, dodecamethylene diisocyanate, cyclohexane-1,3-diisocyanate and cyclohexane-1,4-diisocyanate, 1-isocyanato-3-isocyanatomethyl-3,5,5-trimethylcyclohexane (isophorone diisocyanate or IPDI), bis(4-isocyanatocyclohexyl)-methane, 1,3-bis(isocyanatomethyl)cyclohexane, 1,4-bis(isocyanatomethyl)cyclohexane, bis(4-isocyanato-3-methylcyclohexyl)methane, or mixtures thereof.

In certain embodiments, the diisocyanates are chosen from aliphatic or cycloaliphatic diisocyanates, for example, 1,6-hexamethylene diisocyanate, isophorone diisocyanate, dicyclohexylmethane diisocyanate, or mixtures thereof.

In some embodiments, the use of diols, for example low molecular weight diols, $R_3$, may allow a stiffening of the polymer chain. The expression "low molecular weight diols" means diols having a molecular weight ranging from about 50 to about 800, such as about 60 to 700, or about 62 to 200. They may, in various embodiments, contain aliphatic, alicyclic, or aromatic groups. In certain embodiments, the compounds contain only aliphatic groups. In other embodiments, the diols may have up to about 20 carbon atoms, and may be chosen, for example, from ethylene glycol, diethylene glycol, propane-1,2-diol, propane-1,3-diol, butane-1,4-diol, 1,3-butylene glycol, neopentyl glycol, butylethylpropanediol, cyclohexanediol, 1,4-cyclohexanedimethanol, hexane-1,6-diol, bisphenol A (2,2-bis (4-hydroxyphenyl)propane), hydrogenated bisphenol A (2,2-bis(4-hydroxycyclo-hexyl)propane), or mixtures thereof.

In other embodiments, the low molecular weight diols may contain ionic or potentially ionic groups. Suitable low molecular weight diols containing ionic or potentially ionic groups may be chosen from those disclosed in U.S. Pat. No. 3,412,054, incorporated by reference herein. In various embodiments, compounds may be chosen from dimethylolbutanoic acid (DMBA), dimethylolpropionic acid (DMPA), or carboxyl-containing caprolactone polyester diol. If low molecular weight diols containing ionic or potentially ionic groups are chosen, they may be used in an amount such that less than about 0.30 meq of —COOH is present per gram of polyurethane in the polyurethane dispersion. In certain embodiments, the low molecular weight diols containing ionic or potentially ionic groups are not used.

Reaction product (ii) may be chosen from at least one chain extender according to the formula:

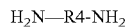

wherein R4 is chosen from alkylene or alkylene oxide radicals, said radicals not being substituted with ionic or potentially ionic groups.

Reaction product (ii) may optionally be chosen from alkylene diamines, such as hydrazine, ethylenediamine, propylenediamine, 1,4-butylenediamine or piperazine; and alkylene oxide diamines such as dipropylamine diethylene glycol (such as DPA-DEG sold by the company Tomah Products), 2-methyl-1,5-pentanediamine (such as Dytec A sold by the company DuPont), hexanediamine, isophoronediamine, and 4,4-methylenedi(cyclohexylamine), and the DPA-series of ether amines available from the company Tomah Products, including dipropylamine propylene glycol, dipropylamine dipropylene glycol, dipropylamine tripropylene glycol, dipropylamine poly(propylene glycol), dipropylamine ethylene glycol, dipropylamine poly(ethylene glycol), dipropylamine 1,3-propanediol, dipropylamine 2-methyl-1,3-propanediol, dipropylamine 1,4-butanediol, dipropylamine 1,3-butanediol, dipropylamine 1,6-hexanediol, dipropylamine cyclohexane-1,4-dimethanol, or mixtures thereof.

Reaction product (iii) may be chosen from at least one chain extender according to the formula:

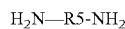

wherein R5 is chosen from alkylene radicals substituted with ionic or potentially ionic groups. In certain exemplary embodiments, the compounds may have an ionic or potentially ionic group and two isocyanate-reactive groups.

As used herein, ionic or potentially ionic groups may include groups comprising ternary or quaternary ammonium groups, groups convertible into such groups, carboxyl groups, carboxylate groups, sulphonic acid groups, and sulphonate groups. At least partial conversion of the groups convertible into salt groups of the type mentioned may take place before or during the mixing with water. Specific compounds include diaminosulphonates, for example the sodium salt of N-(2-aminoethyl)-2-aminoethanesulphonic acid (AAS) or the sodium salt of N-(2-aminoethyl)-2-aminopropionic acid.

In certain embodiments, R5 represents an alkylene radical substituted with sulphonic acid or sulphonate groups. By way of example only, the reaction product (iii) is chosen from sodium salts of N-(2-aminoethyl)-2-aminoethanesulphonic acid.

In certain embodiments, such latexes include, but are not limited to, aqueous polyurethane dispersions comprising a reaction product of a prepolymer comprising a dihydroxyl compound, a polyisocyanate, a low molecular weight diol, at least two diamine compounds, or wherein the composition is substantially free of triethanolamine stearate such as, those sold under the tradename Baycusan® by Bayer such as, Baycusan® C1000 (INCI name: Polyurethane-34), Baycusan® C1001 (INCI name: Polyurethane-34), Baycusan® C1003 (INCI name: Polyurethane-32), Baycusan® C1004 (INCI name: Polyurethane-35) and Baycusan® C1008 (INCI name: Polyurethane-48). In various embodiments, polyurethane latexes may be chosen from, but are not limited to, aqueous polyurethane dispersion of Isophthalic Acid/Adipic Acid/Hexylene Glycol/Neopentyl glycol/Dimethylolpropanoic Acid/Isophorone Diisocyanate copolymer (INCI name: Polyurethane-1, such as Luviset® P.U.R sold by the company BASF), aliphatic polyurethane and aliphatic polyester polyurethane (INCI name: Polycarbamyl Polyglycon Ester such as the Neorez® series sold by the company DSM, including Neorez® R989).

In certain embodiments, the at least two latex polymers may be chosen from polyacrylic latex, polyacrylate latex, polystyrene latex, polyester latex, polyamide latex, polyurea latex, polyurethane latex, epoxy resin latex, cellulose-acrylate latex, or their copolymers.

In various embodiments according to the disclosure, it may be possible to choose a polymer that comprises both acrylate and polyurethane parts at the molecular level.

In one embodiment, the compositions of the present disclosure contain two latex polymers comprising acrylates copolymer as sold under the tradename LUVIFLEX SOFT by BASF and polyurethane-34 as sold under the tradename Baycusan® by Bayer Material Science.

As described herein, certain embodiments according to the disclosure may comprise at least two latex polymers chosen from acrylate and polyurethane polymers, wherein at least one of the latex polymers is a film-forming polymer, with the proviso that when the first latex polymer is chosen from acrylate polymers, the second latex polymer is chosen from polyurethane polymers; and when the first latex polymer is chosen from polyurethane polymers, the second latex polymer is chosen from acrylate polymers.

In certain embodiments, each of the latex polymers is present in an amount ranging from about 0.001% to about 15% by weight, or from 0.05% to about 10% by weight, or from about 0.1% to about 7.5% by weight, or from about 0.25% to about 5% by weight, or from about 0.5% to about 2.5% by weight, or from about 0.5% to about 1.5% by weight, relative to the weight of the composition, including all ranges and subranges therebetween.

In other embodiments, each of the latex polymers is present in an amount ranging from about 1% to about 15% by weight, or from about 1% to about 12% by weight, or from about 1.2% to about 12% by weight, or from about 1.5% to about 10% by weight, or less than about 10% by weight, relative to the weight of the composition, including all ranges and subranges therebetween.

In certain embodiments, the latex polymers are present in a combined amount ranging from about 0.1% to about 30% by weight, or from about about 0.25% to about 20% by weight, or from about 0.3% to about 15% by weight, or from about 0.4% to about 10% by weight, or from about 0.5% to about 5% by weight, relative to the weight of the composition, including all ranges and subranges therebetween.

In other embodiments, the combined amount of latex polymers may be about 0.1%, about 0.5%, about 0.6%, about 0.75%, about 0.9%, about 1%, about 1.5%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, by weight, relative to the weight of the composition.

In further embodiments, the combined amount of latex polymers ranges up to about 30%, up to about 29%, up to about 28%, up to about 27%, up to about 26%, up to about 25%, up to about 24%, up to about 23%, up to about 22%, up to about 21%, up to about 20%, up to about 19%, up to about 18%, up to about 17%, up to about 16%, up to about 15%, up to about 14%, up to about 13%, up to about 12%, up to about 11%, up to about 10%, up to about 10%, up to about 9%, up to about 8%, up to about 7%, up to about 6%, up to about 5%, up to about 4%, up to about 3%, up to about 2%, or up to about 1%, each by weight, relative to the weight of the composition.

In certain embodiments, the combined amount of latex polymers is less than about 10% by weight or less than about 5% by weight, relative to the weight of the composition.

In certain embodiments, the weight ratio of the at least two latex polymers, e.g. polymer A to polymer B, may range from about 10:1 to about 1:10, from about 9:1 to about 1:9, from about 8:1 to about 1:8, from about 7:1 to about 1:7, from about 6:1 to about 1:6, from about 5:1 to about 1:5, from about 4:1 to about 1:4, from about 3:1 to about 1:3, or from about 2:1 to about 1:2.

In other embodiments, the weight ratio of polymer A to polymer B is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10.

According to certain embodiments, when the first latex polymer is chosen from acrylate polymers, and the second latex polymer is chosen from polyurethane polymers, the weight ratio of acrylate polymer to polyurethane polymers is greater than about 1:1, greater than about 2:1, greater than about 3:1, greater than about 4:1, greater than about 5:1, greater than about 6:1, greater than about 7:1, greater than about 8:1, greater than about 9:1, or greater than about 10:1.

In certain embodiments, when polymer A is chosen from latex polymers having a Young's modulus ranging from about 0.1 MPa to about 10 MPa and a strain, under stress at 0.5 MPa, of at least about 1%, and polymer B is chosen from latex polymers having a Young's modulus ranging from about 10 MPa to about 6 GPa and a strain, under stress at 0.5 MPa, of less than about 5%, different weight ratios of polymer A to polymer B may be chosen to correspond to different hair styling applications. In other embodiments, a weight ratio of polymer A to polymer B ranging from about 1:10 to about 1:1 may provide a high level of style hold; a weight ratio of polymer A to polymer B ranging from about 5:1 to about 10:1 may provide a medium to high level of style hold; and a weight ratio of polymer A to polymer B ranging from about 3:1 to about 10:1 may provide a light to medium level of style hold.

Aminofunctional Silicone

The compositions according to the disclosed embodiments comprise at least one aminofunctional silicone.

In certain embodiments, the aminofunctional silicone may be chosen from those having morpholino groups, corresponding to the compounds of formula (I) below:

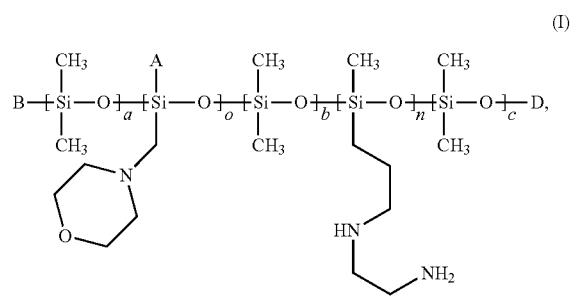

(I)

wherein
A represents —OH, or a structural unit (I), (II), or (III) bound via

—O

(I)

(II)

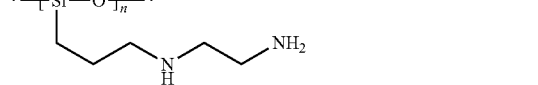

(III)

or an oligomeric or polymeric residue, bound via —O—, containing structural units of formulas (I), (II), or (III), or half of a connecting oxygen atom to a structural unit (III),

* represents a bond to one of the structural units (I), (II), or (III), or denotes a terminal group B (Si-bound) or D (O-bound), B is chosen from an —OH, —O—Si(CH$_3$)$_3$, —O—Si(CH$_3$)$_2$OH, or —O—Si(CH$_3$)$_2$OCH$_3$ group, D is chosen from an —H, —Si(CH$_3$)$_3$, —Si(CH$_3$)$_2$OH, or —Si(CH$_3$)$_2$OCH$_3$ group, a, b, and c represent integers ranging from 0 to 1000, with the provision that a+b+c>0, m, n, and o represent integers ranging from 1 to 1000.

Aminofunctional silicones of this kind bear the INCI name Amodimethicone/Morpholinomethyl Silsesquioxane Copolymer, for example those sold under the tradename Belsil® ADM 6300 E by the company Wacker.

In certain embodiments, the aminofunctional silicone may be chosen from those corresponding to formula (Si-2) below:

$$M(R_aQ_bSiO_{(4-a-b)/2})_x(R_cSiO_{(4-c)/2})_yM \quad \text{(Si-2)};$$

wherein,

R is a hydrocarbon or a hydrocarbon residue having 1 to approximately 6 carbon atoms;

Q is a polar residue of the general formula —$R^1HZ$, wherein $R^1$ is a divalent connecting group that is bound to the hydrogen and to the Z residue, assembled from carbon and hydrogen atoms; carbon, hydrogen, and oxygen atoms; or carbon, hydrogen, and nitrogen atoms, and Z is an organic aminofunctional residue that contains at least one aminofunctional group;

a is a number ranging from about 0 to about 2, b is a number ranging from about 1 to about 3, with the proviso that a+b is less than or equal to 3;

c is a number ranging from about 1 to about 3;

x is a number ranging from about 1 to about 2,000, from about 3 to about 50, or from about 3 to about 25;

y is a number ranging from about 20 to 10,000, from about 125 to about 10,000, or from about 150 to about 1,000; and M is a suitable silicone terminal group known in the existing art, such as trimethylsiloxy.

In other embodiments, Z according to formula (Si-2) may be an organic aminofunctional residue containing at least one functional amino group. In other embodiments, Z may correspond to the formula —$NH(CH_2)_zNH_2$, wherein z is an integer greater than or equal to 1. In other embodiments, Z may correspond to the formula —$NH(CH_2)_z(CH_2)_{zz}NH$, wherein both z and zz, independently of each other, are an integer greater than or equal to 1, and the said structure encompasses diamino ring structures such as piperazinyl. In other embodiments, Z may correspond to the formula —$NHCH_2CH_2NH_2$. In other embodiments, Z may correspond to the formula —$N(CH_2)_z(CH_2)_{zz}NX_2$ or —$NX_2$, wherein each $X_2$ is selected independently from the group consisting of hydrogen and alkyl groups having 1 to 12 carbon atoms, and zz is equal to 0.

In certain embodiments, Q according to formula (Si-2) may be a polar aminofunctional residue corresponding to the formula

—$CH_2CH_2CH_2NHCH_2CH_2NH_2$.

Such silicones are sold under the tradenames Dow Corning (DC) 929 Emulsion, DC2-2078, and DC5-7113, by the company Dow Corning, SM2059 by the company General Electric, and SLM-55067 by the company Wacker.

In certain embodiments, the aminofunctional silicone may be chosen from those cationic aminofunctional silicone polymers corresponding to formula (Si3-a) below:

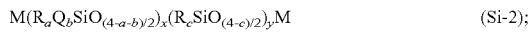

(Si-3a)

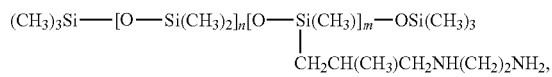

$(CH_3)_3Si\!-\!\![O\!-\!\!Si(CH_3)_2]_n[O\!-\!\!Si(CH_3)]_m\!-\!\!OSi(CH_3)_3$
$\quad\quad\quad\quad\quad\quad\quad\quad\quad |$
$\quad\quad\quad\quad\quad\quad\quad\quad CH_2CH(CH_3)CH_2NH(CH_2)_2NH_2,$ where m and n are numbers whose sum (m+n) ranges from 1 to 2000 or from 50 to 150, where n is a number chosen from 0 to 1999 or from 49 to 149, and m is a number chosen from 1 to 2000 or from 1 to 10.

These silicones are referred to by the INCI name trimethylsilylamodimethicones and are available, for example, under the tradename Q2-7224 by the company Dow Corning.

In certain embodiments, the aminofunctional silicone may be chosen from those corresponding to formula (Si-3b) below:

(Si-3b)

$R\!-\!\![Si(CH_3)_2\!-\!\!O]_{n1}[Si(R')\!-\!\!O]_m\!-\!\![Si(CH_3)_2\!-\!\!O]_{n2}\!-\!\!SiMe_2R$
$\quad\quad\quad\quad\quad\quad\quad\quad\quad\quad |$
$\quad\quad\quad\quad\quad\quad\quad\quad\quad (CH_2)_3NH(CH_2)_2NH_2$

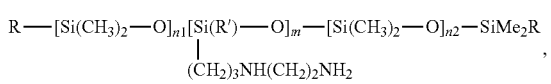

wherein

Me denotes a methyl group,

R may be the same or different, and at least one R is chosen from —OH, a ($C_1$ to $C_{20}$) alkyl group, an ethoxylated and/or propoxylated ($C_1$ to $C_{20}$) alkoxy group, a methoxy group, an ethoxy group, or a —$CH_3$ group, R' is chosen from an —OH, a ($C_1$ to $C_{20}$) alkoxy group, or a —$CH_3$ group, and m, n1, and n2 are numbers whose sum (m+n1+n2) ranges from 1 to 2000 or from 50 to 150, wherein the sum (n1+n2) ranges from 0 to 1999 or from 49 to 149, and m is a number ranging from 1 to 2000 or from 1 to 10.

These silicones are referred to by the INCI name Amodimethicones or as functionalized Amodimethicones, for example Bis(C13-15 Alkoxy) PG Amodimethicone, sold under the tradename DC 8500 by the company Dow Corning, Trideceth-9 PG-Amodimethicone, sold under the tradename Silcare® Silicone SEA by the company Clariant, and Amodimethicone (and) Trideceth-10, sold under the tradename Belsil® ADM 6102 E by the company Wacker, and those sold under the tradenames Wacker Belsil® ADM 652, Wacker Belsil® ADM 653, or Wacker Belsil® ADM 8020 by the company Wacker.

In other embodiments, the aminofunctional silicone may be chosen from polyammonium-polysiloxane compounds, which may be available under the tradename Baysilone®, including Baysilone® TP 3911, SME 253 and SFE 839, by the company GE Bayer Silicones. Polyammonium-polysiloxane compounds can be acquired, for example, from GE Bayer Silicones under the tradename Baysilone®.

According to certain embodiments of the disclosure, the aminofunctional silicone is chosen from those under the INCI name PEG-40/PPG-8 methylaminopropyl/hydroxypropyl dimethicone copolymer sold under the tradename Silsoft® A+ from Momentive, those under the INCI name amodimethicone/morpholinomethyl silsesquioxane copolymer sold under the tradename Belsil® ADM 8301 E from Wacker, an emulsion of amodimethicone/morpholinomethyl silsesquioxane copolymer (and) amodimethicone (and) trideceth-10 (and) acetic acid sold under the tradename Belsil® ADM 6300 E from Wacker, those under the INCI name amodimethicone, or mixtures thereof.

In some embodiments, the at least one aminofunctional silicone chosen from amodimethicone is provided as an emulsion that further comprises surfactants chosen from nonionic or cationic surfactants, or mixtures thereof. Examples of such nonionic surfactants include ethoxylated tridecanol (INCI name: Trideceth-5) and α-isotridecyl-w- hydroxy polyglycol ether (INCI name: Trideceth-10). An example of the cationic surfactant that may be present in the emulsion is cetrimonium chloride. In certain other embodiments, the compositions of the disclosure comprise at least one aminofunctional silicone chosen from amodimethicone which is provided as an emulsion that further comprises nonionic surfactants chosen from trideceth-5, trideceth-10, or mixtures thereof.

In certain embodiments, the at least one aminofunctional silicone is present in an amount ranging from about 0.05% to about 10% by weight, from about 0.1% to about 7.5% by weight, from about 0.2% to about 5% by weight, from about 0.25% to about 3%, or from about 0.5% to about 2.5% by weight, relative to the total weight of the composition, including all ranges and subranges therebetween.

In various embodiments, the total amount of amino functional silicone is about 0.05%, 0.1%, 0.2%, 0.3%, 0.4%, 0.5%, 0.6%, 0.7%, 0.8%, 0.9%, 1%, 1.25%, 1.5%, 2%, 2.5% 3%, 3.5%, 4%, 4.5%, or 5%, by weight, based on the total weight of the composition.

Amphoteric Surfactant

The composition according to the invention comprises one or more amphoteric surfactants (sometimes referred to as zwitterionic surfactants).

The amphoteric surfactant that may be used in the invention may be chosen from optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of (C8-C20)alkylbetaines, sulfobetaines, (C8-C20)alkylsulfobetaines, (C8-C20)alkylamido(C1-C6)alkylbetaines, such as cocamidopropylbetaine, and (C8-C20)alkylamido(C1-C6) alkylsulfobetaines, and mixtures thereof.

Among the optionally quaternized secondary or tertiary aliphatic amine derivatives that may be used, mention may also be made of the products of respective structures (A1) and (A2) below:

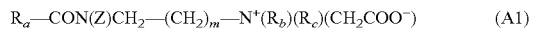

$R_a$—CON(Z)CH$_2$—(CH$_2$)$_m$—N$^+$(R$_b$)(R$_c$)(CH$_2$COO$^-$)      (A1)

wherein:
$R_a$ represents a $C_{10}$-$C_{30}$ alkyl or alkenyl group derived from an acid $R_a$—COOH preferably present in hydrolysed coconut oil, a heptyl group, a nonyl group or an undecyl group,
$R_b$ represents a β-hydroxyethyl group,
$R_c$ represents a carboxymethyl group;
m is equal to 0, 1 or 2,
Z represents a hydrogen atom or a hydroxyethyl or carboxymethyl group;

$R_a$—CON(Z)CH$_2$—(CH$_2$)$_{m'}$—N(B)(B')      (A2)

wherein:
B represents —CH$_2$CH$_2$OX', with X' representing —CH$_2$—COOH, CH$_2$—COOZ', —CH$_2$CH$_2$—COOH, —CH$_2$CH$_2$—COOZ', or a hydrogen atom,
B' represents —(CH$_2$)$_z$—Y', with z=1 or 2, and Y' representing —COOH, —COOZ', —CH$_2$—CHOH—SO$_3$H or —CH$_2$—CHOH—SO$_3$Z',
m' is equal to 0, 1 or 2,
Z represents a hydrogen atom or a hydroxyethyl or carboxymethyl group,
Z' represents an ion resulting from an alkali or alkaline-earth metal, such as sodium, potassium or magnesium; an ammonium ion; or an ion resulting from an organic amine and in particular from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane,
$R_{a'}$ represents a $C_{10}$-$C_{30}$ alkyl or alkenyl group of an acid $R_{a'}$COOH preferably present in hydrolysed linseed oil or coconut oil, an alkyl group, in particular a $C_{17}$ alkyl group, and its iso form, or an unsaturated $C_{17}$ group.

The compounds corresponding to formula (A2) are preferred.

Among the compounds corresponding to formula (A2) in which X' represents an hydrogen atom, mention may be made of compounds classified in the CTFA dictionary, under the names sodium cocoamphoacetate, sodium lauroamphoacetate, sodium caproamphoacetate and sodium capryloamphoacetate.

Other compounds corresponding to formula (A2) are disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

Examples that may be mentioned include the cocoamphodiacetate sold by the company Rhodia under the trade name Miranol® C2M Concentrate, the sodium cocoamphoacetate sold under the trade name Miranol Ultra C 32 and the product sold by the company Chimex under the trade name CHIMEXANE HA.

Use may also be made of the compounds of formula (A3):

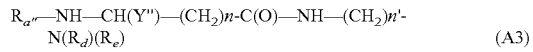

$R_{a''}$—NH—CH(Y'')—(CH$_2$)n-C(O)—NH—(CH$_2$)n'-N(R$_d$)(R$_e$)      (A3)

wherein:
$R_{a''}$ represents a $C_{10}$-$C_{30}$ alkyl or alkenyl group of an acid $R_{a''}$—C(O)OH preferably present in hydrolysed linseed oil or coconut oil;
Y'' represents the group —C(O)OH, —C(O)OZ'', —CH$_2$—CH(OH)—SO$_3$H or the group —CH$_2$—CH (OH)—SO$_3$—Z'', with Z'' representing a cationic counterion resulting from an alkali metal or alkaline-earth metal, such as sodium, an ammonium ion or an ion resulting from an organic amine;
$R_d$ and $R_e$ represent, independently of each other, a C1-C4 alkyl or hydroxyalkyl radical; and
n and n' denote, independently of each other, an integer ranging from 1 to 3.

Among the compounds corresponding to formula (A3), mention may in particular be made of the compound classified in the CTFA dictionary under the name sodium diethylaminopropyl cocoaspartamide, such as the one sold by the company Chimex under the name CHIMEXANE HB.

Preferably, the amphoteric surfactant is chosen from (C8-C20)alkylbetaines, (C8-C20)alkylamido(C1-C6)alkylbetaines, (C8-C20)alkylamphoacetates and (C8-C20)alkylamphodiacetates, and mixtures thereof.

In preferred embodiments of the disclosure, the amphoteric surfactant is chosen from coco-betaine sold by BASF as DEHYTON AB 30

The total amount of amphoteric and/or zwitterionic surfactant present in the composition is from 0.01% to about 5% by weight, from about 0.05% to about 4% by weight, or from about 0.06% to about 3% by weight, relative to the total weight of the composition, including all ranges and subranges therebetween.

In various embodiments, the total amount of amphoteric and/or zwitterionic surfactant is about 0.01%, 0.02%, 0.03%, 0.04%, 0.05%, 0.06%, 0.07%, 0.075%, 0.08%, 0.09%, 0.1%, 0.125%, 0.15%, 0.2%, 0.25% 0.3%, 0.325%, 0.35%, 0.375%, 0.4%, 0.425%, 0.45%, 0.5%, 0.6%, 0.7%, 0.8%, 0.9%, or 1% by weight, relative to the total weight of the composition.

Alykylpolyglucoside

The compositions according to various embodiments of the disclosure can further comprise at least one alkylpolyglucoside.

The alkyl(poly)glucoside (alkylpolyglycoside) in some embodiments is represented by the following general formula:

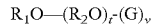

wherein:

$R_1$ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;

$R_2$ represents an alkylene radical comprising 2 to 4 carbon atoms,

G represents a sugar unit comprising 5 to 6 carbon atoms, t denotes a value ranging from 0 to 10 and preferably 0 to 4, v denotes a value ranging from 1 to 15 and preferably 1 to 4.

Preferably, the alkylpolyglycoside surfactant is represented by a compound of the formula described above in which:

$R_1$ denotes a linear or branched, saturated or unsaturated alkyl radical comprising from 8 to 18 carbon atoms, $R_2$ represents an alkylene radical comprising 2 to 4 carbon atoms, t denotes a value ranging from 0 to 3 and preferably equal to 0, G denotes glucose, fructose or galactose, preferably glucose;

the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkyl(poly)glycoside surfactant is an alkyl(poly)glucoside surfactant. C8/C16 alkyl(poly)glucosides 1,4, and especially decyl glucosides and caprylyl/capryl glucosides, are most particularly preferred.

Among the commercial products, mention may be made of the products sold by the company COGNIS under the names PLANTAREN® (600 CS/U, 1200 and 2000) or PLANTACARE® (818, 1200 and 2000); the products sold by the company SEPPIC under the names ORAMIX CG 110 and ORAMIX NS 10; the products sold by the company BASF under the name LUTENSOL GD 70, or else the products sold by the company CHEM Y under the name AG10 LK.

Preferably, use is made of C8/C16-alkyl(poly)glucosides 1,4, especially as an aqueous 53% solution, such as those sold by Cognis under the reference Plantacare® 818 UP.

In an embodiment, the at least one alkylpolyglucoside is chosen from decyl glucoside, stearyl glucoside, lauryl glucoside, coco-glucoside, and mixtures thereof.

In an embodiment, the at least one alkylpolyglucoside is decyl glucoside.

In the present invention, the at least one alkylpolyglucoside may be employed in the composition of the present invention in an amount of from about 0.01% to about 5% by weight, or from about 0.05% to about 4% by weight, or from about 0.08% to about 3% by weight, relative to the total weight of the composition, including all ranges and subranges therebetween.

In various embodiments, the total amount of alkylpolyglucoside is about 0.01%, 0.02%, 0.03%, 0.04%, 0.05%, 0.06%, 0.07%, 0.075%, 0.08%, 0.09%, 0.1%, 0.125%, 0.15%, 0.2%, 0.25% 0.3%, 0.325%, 0.35%, 0.375%, 0.4%, 0.425%, 0.5%, 0.6%, 0.7%, 0.8%, 0.9%, or 1% by weight, based on the total weight of the composition.

Anionic Thickening Agent

The compositions according to the disclosed embodiments comprise at least one anionic thickening agent. Thickening agents can also be referred to interchangeably herein as thickeners or rheology modifiers. A thickening agent is generally used to modify the viscosity and/or rheology of the composition. As used herein, the term "thickening agent" means compounds which, by their presence, increase the viscosity of the composition into which they are introduced by at least 20 cps, such as by at least 50 cps, at 25° C. and at a shear rate of 1 s-1. The viscosity may be measured using a cone/plate viscometer, a Haake R600 rheometer, or the like.

In certain embodiments, the at least one anionic thickening agent may be chosen from those conventionally used in cosmetics, such as polymers of natural origin and synthetic polymers.

In certain embodiments, the anionic thickening agent may be chosen from hydrophilic thickeners. As used herein, the term "hydrophilic thickener" is meant to indicate that the thickening agent is soluble or dispersible in water. Non-limiting examples of hydrophilic thickeners include homopolymers or copolymers of acrylic or methacrylic acids or the salts thereof and the esters thereof, such as those sold under the tradenames Versicol F® or Versicol K® by the company Allied Colloid, or under the tradename Ultrahold 8® by the company Ciba-Geigy; polyacrylates and polymethacrylates such as copolymers of (meth)acrylic acid, copolymers of (meth)acrylic acid, methylacrylate and dimethyl meta-isopropenyl benzyl isocyanate of ethoxylated alcohols such as methylacrylate and dimethyl meta-isopropenyl benzyl isocyanate of ethoxylated alcohol (INCI name: Polyacrylate-3) sold under the tradename Viscophobe® DB 1000 from The Dow Chemical Company, those sold under the tradenames Lubrajel and Norgel by the company Guardian, or under the tradename Hispajel by the company Hispano Chimica; and polyacrylic acids of Synthalen® K type, copolymers of acrylic acid and of acrylamide sold in the form of the sodium salt thereof, such as those sold under the tradenames Reten® by Hercules, sodium polymethacrylate such as those sold under the tradename Darvan® 7 by the company Vanderbilt, and the sodium salts of polyhydroxycarboxylic acids such as those sold under the tradename Hydagen F® by the company Henkel, optionally crosslinked and/or neutralized 2-acrylamido-2-methylpropanesulphonic acid polymers and copolymers, for instance poly(2-acrylamido-2-methylpropanesulphonic acid) such as those sold under the tradename Hostacerin® AMPS (CTFA name: ammonium polyacryldimethyltauramide) by the company Clariant, crosslinked anionic copolymers of acrylamide and of AMPS, e.g. in the form of a water-in-oil emulsion, such as those sold under the tradename Sepigel™ 305 (CTFA name: Polyacrylamide/C13-14 Isoparaffin/Laureth-7) and under the tradename Simugel™ 600 (CTFA name: Acrylamide/Sodium acryloyldimethyltaurate copolymer/Isohexadecane/Polysorbate 80) by the company Seppic, polyacrylic acid/alkyl acrylate copolymers of Pemulen™ type, associative polymers, for instance PEG-150/stearyl alcohol/SMDI copolymer such those as sold under the tradename ACULYN™ 46 by the company Rohm & Haas, steareth-100/PEG-136/HDI copolymer such as those sold under the tradename Rheolate® FX 1100 by the company Elementis, and mixtures thereof.

As used herein, the term "copolymers" is intended to mean both copolymers obtained from two types of monomers and those obtained from more than two types of monomers, such as, for example, terpolymers obtained from three types of monomers. The chemical structure of the copolymers comprises at least one hydrophilic unit and at least one hydrophobic unit. The expression "hydrophobic unit" or "hydrophobic unit" is understood to mean a radical possessing a saturated or unsaturated and linear or branched hydrocarbon-based chain which comprises at least 8 carbon atoms, for example from 10 to 30 carbon atoms, as a further example from 12 to 30 carbon atoms, and as yet a further example from 18 to 30 carbon atoms.

In certain embodiments, the hydrophilic thickener may be chosen from anionic associative polymers. As used herein, the term "associative polymer" is intended to mean any polymer comprising in its structure at least one fatty chain and at least one hydrophilic portion.

In certain embodiments, the associative polymers may be chosen from polymers comprising at least one hydrophilic unit and at least one fatty-chain allyl ether unit; polymers in which the hydrophilic unit is constituted of an ethylenic unsaturated anionic monomer, such as a vinylcarboxylic acid, acrylic acid, methacrylic acid, or mixtures thereof; and polymers in which the fatty-chain allyl ether unit corresponds to the monomer of formula (I) below:

$$CH2=C(R')CH2OB_nR \quad (I)$$

in which R' is chosen from H or CH3, B is an ethyleneoxy radical, n is zero or is chosen from an integer ranging from 1 to 100, and R is a hydrocarbon-based radical chosen from alkyl, arylalkyl, aryl, alkylaryl, or cycloalkyl radicals containing from 8 to 30 carbon atoms, from 10 to 24 carbon atoms, or from 12 to 18 carbon atoms. Exemplary and non-limiting polymers of this type are described and prepared, according to an emulsion polymerization process, in patent EP 0 216 479, incorporated by reference herein.

In certain embodiments, the associative anionic polymer may be chosen from anionic polymers comprising at least one hydrophilic unit of olefinic unsaturated carboxylic acid type, and at least one hydrophobic unit exclusively of (C10 C30)alkyl ester of unsaturated carboxylic acid type.

In certain embodiments, the at least one anionic thickening agent is chosen from copolymers resulting from the polymerization of at least one monomer (a) chosen from carboxylic acids possessing α,β-ethylenically unsaturated groups or their esters, with at least one monomer (b) possessing ethylenically unsaturated groups and comprising a hydrophobic group. Such copolymers may exhibit emulsifying properties.

As used herein, the term "copolymers" is intended to mean both copolymers obtained from two types of monomers and those obtained from more than two types of monomers, such as, for example, terpolymers obtained from three types of monomers. The chemical structure of the copolymers comprises at least one hydrophilic unit and at least one hydrophobic unit. The expression "hydrophobic unit" or "hydrophobic unit" is understood to mean a radical possessing a saturated or unsaturated and linear or branched hydrocarbon-based chain which comprises at least 8 carbon atoms, for example from 10 to 30 carbon atoms, as a further example from 12 to 30 carbon atoms, and as yet a further example from 18 to 30 carbon atoms.

In certain embodiments, the thickening copolymer may be chosen from the copolymers resulting from the polymerization of:

(1) at least one monomer of formula (II):

$$CH2=CH(R1)COOH \quad (II)$$

wherein R1 is chosen from H, CH3, or C2H5, providing acrylic acid, methacrylic acid, or ethacrylic acid monomers, and (2) at least one monomer of (C10 C30)alkyl ester of unsaturated carboxylic acid type corresponding to the monomer of formula (III):

$$CH2=CH(R2)COOR3 \quad (III)$$

wherein R2 is chosen from H, CH3, or C2H5, providing acrylate, methacrylate or ethacrylate units, and R3 denotes a C10 C30 alkyl radical, such as a C12 C22 alkyl radical.

In certain embodiments, the (C10 C30)alkyl esters of unsaturated carboxylic acids may be chosen from lauryl acrylate, stearyl acrylate, decyl acrylate, isodecyl acrylate, dodecyl acrylate or the corresponding methacrylates, such as lauryl methacrylate, stearyl methacrylate, decyl methacrylate, isodecyl methacrylate or dodecyl methacrylate, or mixtures thereof.

In certain embodiments, the crosslinked thickening polymer may be chosen from polymers resulting from the polymerization of a mixture of monomers comprising:

(1) acrylic acid, (2) an ester of formula (III) described above, in which R2 is chosen from H or CH3, R3 denotes an alkyl radical having from 12 to 22 carbon atoms, and (3) a crosslinking agent, which is a known copolymerizable polyethylenic unsaturated monomer, such as diallyl phthalate, allyl (meth)acrylate, divinylbenzene, (poly)ethylene glycol dimethacrylate and methylenebisacrylamide.

In various embodiments, the crosslinked thickening polymer may comprise from about 60% to about 95% by weight of acrylic acid (hydrophilic unit), from about 4% to about 40% by weight of C10 C30 alkyl acrylate (hydrophobic unit), and from about 0% to about 6% by weight of crosslinking polymerizable monomer. In further embodiments, the crosslinked thickening polymer may comprise from about 96% to about 98% by weight of acrylic acid (hydrophilic unit), from about 1% to about 4% by weight of C10 C30 alkyl acrylate (hydrophobic unit), and from about 0.1% to 0.6% by weight of crosslinking polymerizable monomer, such as those described above.

In some embodiments, the crosslinked thickening polymer may be chosen from acrylate/C10 C30 alkyl acrylate copolymers (INCI name: Acrylates/C10-30 Alkyl Acrylate Crosspolymer), such as the products sold under the tradenames Pemulen™ TR1, Pemulen™ TR2, Carbopol® 1382 and Carbopol® EDT 2020 by the company Lubrizol.

In certain embodiments, the anionic thickening agent may be chosen from gellifying agents and/or viscosity modifying agents.

The anionic thickening agent of the present disclosure may also be chosen from rheology modifiers such as acrylate- or acrylic-based polymers, carbomers, crosslinked homopolymers of acrylic acid or of acrylamidopropanesulfonic acid, and crosslinked copolymers of (meth)acrylic acid and/or (C1-C6)alkyl esters.

In an embodiment, the anionic thickening agent is chosen from polyacrylate-3, commercially known under the trade name of Viscophobe DB-100 and sold by The Dow Chemical Company, carbomers, commercially known under the trade name of Carbopol polymers and sold by Lubrizol Advance Materials, Inc, acrylates/C10-30 alkyl acrylate crosspolymers, commercially known the trade names of Pemulen TR-1 and Pemulen TR-2 polymers and sold by Lubrizol Advance Materials, Inc, Acrylates/C10-30 Alkyl Acrylate Crosspolymer such as Carbopol® Ultrez 20 Polymer by and sold by Lubrizol Advance Materials, Inc, AMP-acrylates/allyl methacrylate copolymer, commercially known under the trade name of Fixate G-100 polymer and sold by Lubrizol Advance Materials, Inc., Polyacrylate Crosspolymer-6 such as Sepimax™ Zen by the company Seppic, and a crosslinked methacrylic acid/ethyl acrylate copolymer, also known as an acrylates copolymer in aqueous dispersion, such as the slightly cross-linked, alkali-swellable acrylate polymer known by the INCI name acrylates copolymer and sold by Lubrizol, under the tradename CARBOPOL Aqua SF-1 as an aqueous dispersion comprising about 30 percent by weight of total solids or active material.

According to various embodiments, the total amount of anionic thickening agent ranges from about 0.01% to about 15% by weight, or from about 0.01% to about 10% by weight, or from about 0.05% to about 5% by weight, or from about 0.1% to about 5% by weight, or from about 0.1% to about 3% by weight, or from about 0.3% to about 2% by weight, relative to the total weight of the composition, including all ranges and subranges therebetween In various embodiments, the anionic thickening agent may be present in a total amount of about 0.01%, 0.02%, 0.03%, 0.04%, 0.05%, 0.06%, 0.07%, 0.075%, 0.08%, 0.09%, 0.1%, 0.125%, 0.15%, 0.2%, 0.25% 0.3%, 0.325%, 0.35%, 0.375%, 0.4%, 0.425%, 0.45%, 0.5%, 0.55%, 0.6%, 0.65%, 0.7%, 0.75%, 0.8%, 0.85%, 0.9%, 0.95%, 1%, 1.5%, 2%, 2.5%, or 3% A by weight, relative to the total weight of the composition.

Neutralizing Base

In certain embodiments, the at least one anionic thickening agent is generally neutralized before being included in, or as it is, added to the compositions of the disclosure. The anionic thickening agent may be neutralized by employing traditional neutralizing agents, also known as neutralizing bases. As used herein, a "neutralizing base" is an alkaline compound that partially or totally neutralizes the negative charge of the anionic thickener.

According to some embodiments of the disclosure, the composition comprises at least two different alkaline components employed as neutralizing bases.

Nonlimiting examples of neutralizing bases include hydroxide-containing compounds chosen from alkali metal hydroxides, alkaline-earth metal hydroxides, transition metal hydroxides such as sodium hydroxide, potassium hydroxide, lithium hydroxide, calcium hydroxide, magnesium hydroxide, barium hydroxide, strontium hydroxide, manganese hydroxide, and zinc hydroxide; ammonia; organic amines such as monoethanolamine, diethanolamine, triethanolamine, N-methylglucamine, aminomethyl propanol, aminomethyl propanediol, ethoxylated amines, PEG-25 cocamine, polyoxyethylene (5) cocamine, polyoxyethylene (25) cocamine, polyoxyethylene (5) octadecylamine, polyoxyethylene (25) octadecylamine, polyoxyethylene (5) tallowamine, polyoxyethylene (I5) oleylamine, polyethylene (5) soyamine, and polyoxyethylene (25) soyamine; basic amino acids such as arginine and lysine; and mixtures thereof.

According to some embodiments, the neutralizing base is chosen from aminomethyl propanol and triethanolamine.

In certain embodiments, a first neutralizing base and a second neutralizing base are added to the composition at different times. According to some embodiments, a first neutralizing base is added to the composition including an anionic thickener, and a second neutralizing base is added to the composition at a later time. In some embodiments, the first neutralizing base is triethanolamine and the second neutralizing base is aminomethyl propanol.

According to various embodiments of the disclosure, the addition of at least two neutralizing bases will slightly thicken the composition. Without wishing to be bound by theory, in some embodiments a slightly thickened composition may provide a foam having better structure and/or better stability.

In certain embodiments, each of the neutralizing bases is present in an amount ranging from about 0.001% to about 10% by weight, from 0.005% to about 5% by weight, from about 0.01% to about 3% by weight, from about 0.05% to about 2% by weight, from about 0.05% to about 1% by weight, from about 0.05% to about 0.5% by weight, from about 0.1% to about 1.5% by weight, or from about 0.2% to about 1.0% by weight, relative to the weight of the composition.

In certain embodiments, the neutralizing bases are present in a combined amount ranging from 0.001% to about 10% by weight, from 0.005% to about 8% by weight, from about 0.01% to about 6% by weight, from about 0.05% to about 5% by weight, from about 0.1% to about 3% by weight, from about 0.15% to about 1.0% by weight, or from about 0.2% to about 1.0% by weight, relative to the weight of the composition.

In other embodiments, the combined amount of neutralizing bases may be about 0.1%, about 0.15%, about 0.2%, about 0.25%, about 0.3%, about 0.4%, about 0.5%, about 0.6%, about 0.7%, about 0.8%, about 0.9%, about 1.0%, about 2%, about 3%, or about 4% by weight, relative to the weight of the composition.

Additional Thickening Agents/Rheology Modifier

The compositions according to the disclosed embodiments may further comprise an additional thickening agent, also referred to interchangeably herein as thickener or rheology modifier.

In certain embodiments, the additional thickening agent may be chosen from those conventionally used in cosmetics, such as polymers of natural origin and synthetic polymers, for example, nonionic, anionic, cationic, amphiphilic, or amphoteric polymers, and other known rheology modifiers, such as cellulose-based thickeners.

In certain embodiments, additional the thickening agent may be chosen from hydrophilic thickeners, for example cellulose polymers and gums, modified or unmodified carboxyvinyl polymers, such as those sold under the tradename Carbopol® (CTFA name: carbomer) by the company Goodrich, polyacrylamides, copolymers of acrylic acid and of acrylamide sold in the form of the sodium salt thereof, such as those sold under the tradenames Reten® by Hercules, and the sodium salts of polyhydroxycarboxylic acids such as those sold under the tradename Hydagen F® by the company Henkel, optionally crosslinked and/or neutralized 2-acrylamido-2-methylpropanesulphonic acid polymers and copolymers, for instance poly(2-acrylamido-2-methylpropanesulphonic acid) such as those sold under the tradename Hostacerin® AMPS (CTFA name: ammonium polyacryldimethyltauramide) by the company Clariant, cross-linked anionic copolymers of acrylamide and of AMPS, e.g.

in the form of a water-in-oil emulsion, such as those sold under the tradename Sepigel™ 305 (CTFA name: Polyacrylamide/C13-14 Isoparaffin/Laureth-7) and under the tradename Simugel™ 600 (CTFA name: Acrylamide/Sodium acryloyldimethyltaurate copolymer/Isohexadecane/Polysorbate 80) by the company Seppic, polyacrylic acid/alkyl acrylate copolymers of Pemulen™ type, associative polymers, for instance PEG-150/stearyl alcohol/SMDI copolymer such those as sold under the tradename ACULYN™ 46 by the company Rohm & Haas, steareth-100/PEG-136/HDI copolymer such as those sold under the tradename Rheolate® FX 1100 by the company Elementis, and mixtures thereof.

In certain embodiments, the hydrophilic thickener may be chosen from associative polymers. As used herein, the term "associative polymer" is intended to mean any amphiphilic polymer comprising in its structure at least one fatty chain and at least one hydrophilic portion. As used herein, the term "amphiphilic polymer" means a polymer composed of hydrophilic and hydrophobic parts.

In certain embodiments, the associative polymer may be anionic, cationic, nonionic, or amphoteric. In certain embodiments, the associative polymer may be chosen from polymers comprising at least one hydrophilic unit and at least one fatty-chain allyl ether unit; polymers in which the hydrophilic unit is constituted of an ethylenic unsaturated anionic monomer, such as a vinylcarboxylic acid, acrylic acid, methacrylic acid, or mixtures thereof; and polymers in which the fatty-chain allyl ether unit corresponds to the monomer of formula (I) below:

$$CH_2=C(R')CH_2OB_nR \quad (I)$$

in which R' is chosen from H or $CH_3$, B is an ethyleneoxy radical, n is zero or is chosen from an integer ranging from 1 to 100, and R is a hydrocarbon-based radical chosen from alkyl, arylalkyl, aryl, alkylaryl, or cycloalkyl radicals containing from 8 to 30 carbon atoms, from 10 to 24 carbon atoms, or from 12 to 18 carbon atoms. Exemplary and non-limiting polymers of this type are described and prepared, according to an emulsion polymerization process, in patent EP 0 216 479, incorporated by reference herein.

In other embodiments, the associative cationic polymer may be chosen from quaternized cellulose derivatives and polyacrylates containing amine side groups.

In other embodiments, the non-ionic associative polymer may be chosen from celluloses modified with groups comprising at least one fatty chain, for instance hydroxyethyl celluloses modified with groups comprising at least one fatty chain, such as alkyl groups, e.g. $C_8$-$C_{22}$ alkyl groups, arylalkyl and alkylaryl groups; cetyl hydroxyethyl cellulose, also known under the tradename Natrosol® Plus (sold by the company Ashland), Bermocoll EHM 100 (sold by the company Berol Nobel), Amercell Polymer HM-1500® sold by the company Amerchol; hydroxyethylcellulose modified with a polyethylene glycol (15) nonylphenyl ether group, sold by the company Amerchol; celluloses modified with polyalkylene glycol alkylphenyl ether groups; guars such as hydroxypropyl guar, optionally modified with groups comprising at least one fatty chain such as an alkyl chain, for example Jaguar® XC-95/3 (C14 alkyl chain, sold by the company Rhodia Chimie), Esaflor HM 22 (C22 alkyl chain, sold by the company Lamberti), RE210-18 (C14 alkyl chain) and RE205-1 (C20 alkyl chain, sold by the company Rhodia Chimie); copolymers of vinylpyrrolidone and of fatty-chain hydrophobic monomers, for instance Antaron® or Ganex® V216 (vinylpyrrolidone/hexadecene copolymers), Antaron® or Ganex® V220 (vinylpyrrolidone/eicosene copolymers) sold by the company I.S.P.; copolymers of $C_1$-$C_6$ alkyl methacrylates, acrylates or amphiphilic monomers comprising at least one fatty chain; or copolymers of hydrophilic methacrylates, acrylates or hydrophobic monomers comprising at least one fatty chain, for instance the polyethylene glycol methacrylate/lauryl methacrylate copolymer.

An associative polyurethane may also be chosen in various embodiments. As used herein, "associative polyurethanes" are nonionic block copolymers comprising in the chain both hydrophilic blocks usually of polyoxyethylene nature, and hydrophobic blocks that may be aliphatic sequences alone and/or cycloaliphatic and/or aromatic sequences. Associative polyurethanes comprise at least two hydrocarbon-based lipophilic chains containing from $C_6$ to $C_{30}$ carbon atoms, separated by a hydrophilic block, the hydrocarbon-based chains optionally being pendent chains or chains at the end of a hydrophilic block. For example, it is possible for one or more pendent chains to be provided. In addition, the polymer may comprise a hydrocarbon-based chain at one or both ends of a hydrophilic block. The associative polyurethanes may be arranged in triblock or multiblock form. The hydrophobic blocks may thus be at each end of the chain (for example, triblock copolymer with a hydrophilic central block) or distributed both at the ends and within the chain (for example, multiblock copolymer). These polymers may also be graft polymers or starburst polymers. In one embodiment, the associative polyurethanes may be triblock copolymers in which the hydrophilic block is a polyoxyethylene chain containing from 50 to 1000 oxyethylene groups.

In other embodiments, associative polymers of the polyurethane polyether type that may be used include the polymer $C_{16}$-$OE_{120}$-$C_{16}$ from Servo Delden (under the tradename SER AD FX1100), which is a molecule containing a urethane function and having a weight-average molecular weight of 1300, OE being an oxyethylene unit; Nuvis® FX 1100 (European and US INCI name "Steareth-100/PEG-136/HMDI Copolymer" sold by the company Elementis Specialties); Acrysol RM 184® (sold by the company Rohm and Haas); Elfacos® T210® (C12-C14 alkyl chain); Elfacos® T212® (C18 alkyl chain) sold by the company Akzo; Rheolate® 205 containing a urea function, sold by the company Rheox; RHEOLATE® 208 or 204, or RHEOLATE® FX1100 sold by the company Elementis; or DW 1206B sold by the company Rohm & Haas containing a $C_{20}$ alkyl chain with a urethane bond, sold at a solids content of 20% in water.

In further embodiments, solutions or dispersions of these polymers, especially in water or in aqueous-alcoholic medium, may be chosen. Examples of such polymers include SER AD FX1010, SER AD FX1035, and SER AD 1070 from the company Servo Delden, and Rheolate® 255, Rheolate® 278, and Rheolate® 244 sold by Rheox. Further examples include the products Aculyn™ 46, DW 1206F, and DW 1206J, Acrysol RM 184 or Acrysol 44 from the company Rohm & Haas, and Borchi® Gel LW 44 from the company Borchers.

In further embodiments, the additional thickening agent may be chosen from nonionic homopolymers or copolymers containing ethylenically unsaturated monomers of the amide type, for example, the polyacrylamide products sold under the tradenames Cyanamer® P250 by the company CYTEC.

In further embodiments, the additional thickening agent chosen from polymers of natural origin may include thickening polymers comprising at least one sugar unit, for instance nonionic guar gums, optionally modified with C1-C6 hydroxyalkyl groups; biopolysaccharide gums of microbial origin, such as scleroglucan gum (also known as *sclerotium* gum) or xanthan gum; gums derived from plant exudates, such as gum arabic, ghatti gum, karaya gum, gum tragacanth, carrageenan gum, agar gum, carob gum, *ceratonia siliqua* gum or *cyamopsis tetragonoloba* (guar) gum; pectins; alginates; starches; hydroxy(C1-C6)alkylcelluloses; or carboxy(C1-C6)alkylcelluloses.

In certain embodiments, the nonionic, unmodified guar gums may be chosen from Guargel D/15 sold by the company Noveon, Vidogum GH 175 sold by the company Unipectine, Meypro-Guar 50 sold by the company Meyhall, or Jaguar® C sold by the company Rhodia Chimie. In other embodiments, the nonionic modified guar gums may be chosen from Jaguar® HP8, HP60, HP120, DC 293 and HP 105 sold by the companies Meyhall and Rhodia Chimie or Galactasol™ 4H4FD2 sold by the company Ashland.

In other embodiments, the additional thickening agent may be chosen from scleroglucans, for example, Actigum™ CS from Sanofi Bio Industries; Amigel® sold by the company Alban Muller International; xanthan gums, for instance Keltrol®, Keltrol® T, Keltrol® Tf, Keltrol® Bt, Keltrol® Rd, and Keltrol® Cg sold by the company CP Kelco, Rhodicare® S and Rhodicare® H sold by the company Rhodia Chimie; starch derivatives, for instance Primogel® sold by the company Avebe; hydroxyethylcelluloses such as Cellosize® QP3L, QP4400H, QP30000H, HEC30000A and Polymer PCG10 sold by the company Amerchol, Natrosol™ 250HHR, 250MR, 250M, 250HHXR, 250HHX, 250HR, and 250 HX, sold by the company Hercules, or Tylose® H1000 sold by the company Hoechst; hydroxypropylcelluloses, for instance Klucel™ EF, H, LHF, MF, and G, sold by the company Ashland; carboxymethylcelluloses, for instance Blanose® 7M8/SF, refined 7M, 7LF, 7MF, 9M31F, 12M31XP, 12M31P, 9M31XF, 7H, 7M31, and 7H3SXF, sold by the company Ashland, Aquasorb® A500 sold by the company Hercules, Ambergum® 1221 sold by the company Hercules, Cellogen® HP810A and HP6HS9 sold by the company Montello and Primellose® sold by the company Avebe.

In other embodiments, the modified nonionic guar gums may, for example, be modified with C1-C6 hydroxyalkyl groups. Such hydroxyalkyl groups may be chosen from hydroxymethyl, hydroxyethyl, hydroxypropyl, and hydroxybutyl groups.

In certain embodiments, guar gums may be prepared by reacting the corresponding alkylene oxides, such as for example propylene oxides, with guar gum so as to obtain a guar gum modified with hydroxypropyl groups. The hydroxyalkylation ratio, which corresponds to the number of alkylene oxide molecules consumed to the number of free hydroxyl functional groups present on the guar gum, may in certain embodiments range from about 0.4 to about 1.2.

Examples of nonionic guar gums, optionally modified with hydroxyalkyl groups, include those sold under the tradenames Jaguar® HP8, Jaguar® HP60, Jaguar® HP120, Jaguar® DC 293, and Jaguar® HP 105 by the company Rhodia Chimie, and under the tradename Galactasol™ 4H4FD2 by the company Ashland.

In other embodiments, the guar gum may be chosen from those modified with a quaternary ammonium group, such as guar hydroxypropyltrimonium chloride, also sold under the tradename Jaguar® C-13S by the company Rhodia Chimie.

In other embodiments, the celluloses may be chosen from hydroxyethylcelluloses and hydroxypropylcelluloses, such as those sold under the tradenames Klucel™ EF, Klucel™ H, Klucel™ LHF, Klucel™ MF, Klucel™ G, by the company Ashland and under the tradename Cellosize™ PCG-10 by the company Amerchol.

In other embodiments, non-limiting thickening polysaccharides may be chosen from glucans; modified or unmodified starches such as those derived, for example, from cereals such as wheat, corn or rice, vegetables such as golden pea, or tubers such as potato or cassava; amylose, amylopectin, glycogen, dextrans, celluloses or derivatives thereof (methylcelluloses, hydroxyalkylcelluloses, ethylhydroxyethylcelluloses), mannans, xylans, lignins, arabans, galactans, galacturonans, chitin, chitosans, glucoronoxylans, arabinoxylans, xyloglucans, glucomannans, pectic acids or pectins, arabinogalactans, carrageenans, agars, gums arabic, gums tragacanth, Ghatti gums, Karaya gums, carob gums, galactomannans such as guar gums and their nonionic derivatives such as hydroxypropylguar, or mixtures thereof.

In certain embodiments, the additional thickening agent may be chosen from silicas or hydrophobic silicas, such as those described in EP-A-898960, incorporated by reference herein. Examples of such silicas include those sold under the tradename Aerosil® R812 by the company Degussa, CAB-O-SIL® TS-530, CAB-O-SIL® TS-610, CAB-O-SIL® TS-720 by the company Cabot, or Aerosil® R972 and Aerosil® R974 by the company Degussa; clays, such as montmorillonite; modified clays such as the bentones, for example, stearalkonium hectorite, stearalkonium bentonite; or polysaccharide alkyl ethers, optionally with the alkyl group having from 1 to 24 carbon atoms, for example from 1 to 10 carbon atoms, from 1 to 6 carbon atoms, or from 1 to 3 carbon atoms, such as those described in document EP-A-898958, incorporated by reference herein.

The additional thickening agent of the present disclosure may be chosen from rheology modifiers such as crosslinked homopolymers of acrylamidopropane-sulfonic acid.

Non-limiting examples of the additional thickening agent include Polyacrylamide (and) C13-14 Isoparaffin (and) Laureth-7 such as Sepigel™ 305 by the company Seppic, Hydroxypropyl Guar such as Jaguar® HP105 by the company Rhodia, *Cyamopsis Tetragonoloba* (Guar) Gum such as Supercol® U Guar Gum by the company Ashland, *Sclerotium* Gum such as Amigum by the company Alban Muller, Xanthan Gum (and) *Ceratonia Siliqua* Gum such as Nomcort CG by the company Nisshin Oil Lio, Hydroxypropyl Guar such as Jaguar® HP8 by the company Rhodia, Guar Hydroxypropyl Trimonium Chloride such as Jaguar® C-13-S by the company Rhodia, or Hydroxyethyl Cellulose such as Natrosol™ 250 MR by the company Ashland.

In certain embodiments, the additional thickening agent may be chosen from non-associative cationic polymers In certain embodiments, the additional thickening agent may be chosen from gellifying agents and/or viscosity modifying agents.

In one embodiment, the additional thickening agent is chosen from xanthan gum, guar gum, hydroxypropyl guar, guar hydroxypropyl trimonium chloride, hydroxyethyl cellulose, hydroxypropyl cellulose, cetyl hydroxyethyl cellulose, or mixtures thereof.

In various embodiments, the additional thickening agent may be present in an amount ranging from about 0.01% to about 15% by weight, or from about 0.05% to about 5% by weight, or from about 0.1% to about 5% by weight, or from about 0.1% to about 3% by weight, or from about 0.3% to about 2% by weight, relative to the total weight of the composition, including all ranges and subranges therebetween.

In various embodiments, the additional thickening agent may be present in an amount of about 0.01%, 0.02%, 0.03%, 0.04%, 0.05%, 0.06%, 0.07%, 0.075%, 0.08%, 0.09%, 0.1%, 0.125%, 0.15%, 0.2%, 0.25% 0.3%, 0.325%, 0.35%, 0.375%, 0.4%, 0.425%, 0.45%, 0.5%, 0.55%, 0.6%, 0.65%, 0.7%, 0.75%, 0.8%, 0.85%, 0.9%, 0.95%, 1%, 1.5%, 2%, 2.5%, or 3% by weight, relative to the total weight of the composition.

Coalescing Agents and Plasticizers

The compositions according to the disclosed embodiments may optionally comprise at least one component chosen from coalescing agents and plasticizers. Without wishing to be bound by theory, it is believed that the addition of at least one coalescing agent and/or plasticizer may lower the glass transition temperature (Tg), decrease the Young's modulus, and/or increase the strain of latex polymers and/or the films formed by latex polymers. Further, the at least one coalescing agent and/or plasticizer may also be used to aid coating formation of the latex film to form a continuous and homogeneous film or coating and to improve adhesion. While the lowering of the Tg of the latex polymers can result in a softening of the film or coating formed by the latex polymers, it has been found that the coating or film produced on hair treated with the compositions of the disclosure imparts a stronger styling hold to the hair and a more balanced coating or film.

In various embodiments, the at least one coalescing agent and/or plasticizer may be chosen from glycols and their derivatives, such as glycol ethers, for example, ethylene glycol, propylene glycol, diethylene glycol ethyl ether, diethylene glycol methyl ether, diethylene glycol butyl ether, diethylene glycol hexyl ether, diethylene glycol dibutyl ether, ethylene glycol methyl ether, ethylene glycol ethyl ether, ethylene glycol butyl ether, or ethylene glycol hexyl ether; glycol esters, such as diethylene glycol butyl ether acetate, propylene glycol dibenzoate or dipropylene glycol dibenzoate; cellulose esters, such as sucrose acetate; propylene glycol derivatives, such as propylene glycol phenyl ether, propylene glycol diacetate, dipropylene glycol butyl ether, tripropylene glycol butyl ether, propylene glycol methyl ether, dipropylene glycol ethyl ether, tripropylene glycol methyl ether, diethylene glycol methyl ether, or propylene glycol butyl ether.

In other embodiments, the coalescing agent and/or plasticizer may be chosen from acid esters, such as carboxylic acid esters. In other embodiments, the component chosen from coalescing agent and plasticizer may be chosen from acetates, such as glycerol triacetate; citrates, such as triethyl citrate, tributyl citrate, triethyl acetylcitrate, tributyl acetylcitrate, or tri(2-ethylhexyl)acetylcitrate; phthalates, such as diethyl phthalate, dibutyl phthalate, dioctyl phthalate, dipentyl phthalate, dimethoxyethyl phthalate, butyl phthalate, or 2-ethylhexyl phthalate; phosphates, such as tricresyl phosphate, tributyl phosphate, triphenyl phosphate, or tributoxyethyl phosphate; tartrates, such as dibutyl tartrate; or sebacates, such as dimethyl sebacate or dibutyl sebacate.

In other embodiments, the coalescing agent and/or plasticizer may be chosen from, fatty acid esters, such as adipic acid esters, for example, diisobutyl adipate or diethyl adipate; stearic acid esters, such as ethyl stearate; or palmitic acid esters, such as 2-ethylhexyl palmitate, succinates, abietates, caprylates, caproates, enanthates, or myristates.

In further embodiments, the coalescing agent and/or plasticizer may be chosen from carbonates, such as ethylene carbonate or propylene carbonate; benzyl benzoate, sucrose benzoate, butyl acetylricinoleate, glyceryl acetylricinoleate, butyl glycolate, camphor, N-ethyl-o,p-toluenesulphonamide, or ethyl tosylamide.

In further embodiments, the coalescing agent and/or plasticizer may be chosen from compounds comprising at least one fatty acid chosen from caprylic acid, capric acid, lauric acid, myristic acid, palmitic acid, stearic acid, oleic acid, ricinoleic acid, linoleic acid, linolenic acid, arachidic acid, gadoleic acid, behenic acid, erucic acid, brassidic acid, cetoleic acid, lignoceric acid, or nervonic acid.

In further embodiments, the coalescing agent and/or plasticizer may be chosen from alcohols such as hexanol and benzyl alcohol.

In certain embodiments, the coalescing agent and/or plasticizer may be chosen from propylene glycol dibenzoate, sold under the tradename Lexfeel® Shine by the company Inolex, dipropylene glycol dibenzoate, sold under the tradename Dermol DPG-2b by the company Alzo, and propylene glycol butyl ether, sold under the tradename Dowanol™ PnB by the company Dow Chemical.

It should be understood that mixtures of the above agents may be used according to various embodiments.

In various embodiments, the at least one component chosen from coalescing agents and/or plasticizers may be present in an amount ranging from about 0.1% to about 20% by weight, from about 0.1% to about 10% by weight, or from about 0.1% to about 5% by weight, with respect to the total weight of the composition.

In various embodiments, the at least one component chosen from coalescing agents and/or plasticizers may be present in an amount ranging from about 0.1% to about 2% by weight or from about 0.1% to about 1% by weight, with respect to the total weight of the composition.

In other embodiments, compositions of the disclosure may comprise at least one water-soluble resin such as polyethylene oxide having a molecular weight ranging from about 100,000 to about 10,000,000. Examples of such polyethylene oxides include, but are not limited to, Polyox water-soluble resins manufactured by the company Dow under the INCI names of PEG-2M, PEG-5M, PEG-7M, PEG-14M, PEG-23M, PEG-45M, PEG-90M, PEG-160M, and PEG-180M. PEG-90M is known under the tradename Polyox™ WSR 301 and PEG-45M is known under the tradename Polyox™ WSR 60k. The amounts of water-soluble resins in the compositions, when present, may range from about 0.1% to about 2% by weight, relative to the total weight of the composition.

It is to be understood that any combination of the above mentioned agents is contemplated according to various exemplary embodiments of the disclosure.

Solvent

The compositions according to the disclosed embodiments may further comprise at least one solvent. In certain embodiments, the at least one solvent may be chosen from water, at least one cosmetically acceptable organic solvent, or a mixture of water and at least one cosmetically acceptable organic solvent. In various embodiments, the cosmetically acceptable organic solvents may be water-miscible, e.g. a mixture capable of forming at 25° C. a homogeneous mixture that is transparent, or substantially transparent, to the eye, chosen from lower monoalcohols, such as those containing from about 1 to 5 carbon atoms, for example ethanol and isopropanol; polyols, including glycols, such as those containing from about 2 to 8 carbon atoms, for example propylene glycol, ethylene glycol, 1,3-butylene glycol, dipropylene glycol, hexylene glycol, and glycerin; hydrocarbons, such as, for example, isododecane and mineral oil; silicones, such as dimethicones, cyclomethicones, trisiloxane, and cyclopentasiloxane; or mixtures thereof.

In certain embodiments, the latex polymer particles are not soluble in the solvent of the composition, and thus remain in particulate form while in the composition and after evaporation of the solvent. For example, in embodiments where the composition comprises alcohol as a cosmetically acceptable organic solvent, the latex particles may remain in particulate form upon evaporation of the alcohol, such as once the composition is applied to a substrate.

According to various embodiments, the at least one solvent may be present in an amount ranging up to about 95% by weight, from about 1% to about 90% by weight, or from about 5% to about 80% by weight, relative to the total weight of the composition.

Propellant

The compositions according to the disclosed embodiments may further comprise at least one propellant. As used herein, the term "propellant" is meant to indicate a liquid or gas that is packaged with the composition in a device under pressure, which serves to dispense the composition from the device with force and/or facilitate or enhance the foaming of the composition.

Nonlimiting examples of propellants that are suitable for use include gases usually used in the cosmetic field, in particular optionally halogenated volatile hydrocarbons, for example n-butane, propane, isobutane, or pentane, and halogenated derivatives thereof; carbon dioxide, nitrous oxide, dimethyl ether, hydrofluorocarbons, and nitrogen, alone or as mixtures.

In certain embodiments of the disclosure, the propellant is chosen from alkanes and in particular from n-butane, propane, and isobutane, and mixtures thereof.

According to various embodiments, the propellant is under pressure, and at least partially in liquid form.

In certain embodiments, the total amount of propellant ranges from about 1% to about 30% by weight, relative to the weight of the composition, such as from about 2% to about 15% by weight relative to the weight of the composition.

Compositions

The compositions according to the disclosed embodiments may further comprise additional components that are typically used in hair styling compositions. Such components are known to those of skill in the art, or are within the ability of those of skill in the art to determine depending on the particular application, such as, for example, organic amines, carbonate compounds, emulsifying agents, fillers, pigments, conditioning agents, moisturizing agents, additional viscosity or thickening agents, shine agents, sequestering agents, fragrances, preservatives, pH modifiers/neutralizing agents, stabilizers, propellants, or mixtures thereof.

In various embodiments, the composition described herein may have a pH ranging from about 2 to about 9, such as about 3 to about 8, or about 5 to about 7.

In some embodiments, the compositions are in the form of hair styling compositions, in any form, such as, for example, a gel, a foam, a lotion, an emulsion, or a liquid that may be sprayed onto or otherwise applied to the hair. In certain exemplary embodiments, the composition may be provided in the form of a mousse, or a spray.

In various embodiments, the composition is a hair styling composition. According to various embodiments, by "hair styling composition" the composition is meant to be applied to hair on the head other than eyelashes and/or eyebrows. Hair styling compositions and mascaras are sometimes distinguishable based on the components of the compositions and/or the effects of the compositions when applied. In some embodiments, at least one component of a hair styling composition is not compatible for use in a mascara. In other embodiments, at least one component of a mascara is not compatible for use in a hair styling composition.

According to some embodiments, the composition is not applied to the eyelashes and/or eyebrows. In certain embodiments, the composition is not a mascara.

In certain embodiments, the composition may be applied to the hair by first applying to the hands, and then contacting the hair with the hands. In other embodiments, the composition may be applied directly onto the hair, such as by spraying. In other embodiments, the composition may be applied to wet or dry hair. The compositions may, in various embodiments, be applied to the hair as a leave-on treatment.

In one embodiment, the hair is allowed to air dry after application of the composition, and no heat is applied to the hair.

In one embodiment, the hair is allowed to air dry after application of the composition, and is styled or shaped with no heat being applied to the hair.

Styling or shaping the hair may involve the use of devices on hair such as a brush, a comb or running the fingers of the hand through the hair.

In various embodiments, the application of an external stimuli, such as heat, may be desirable as part of the hair styling process. By way of example only, before, during, or after the composition is applied to wet or dry hair, the hair may optionally be further treated with an external stimuli, for example with heat ranging from about 25° C. to about 250° C. In at least certain embodiments, the hair may also be shaped or positioned as desired while exposed to external stimuli, such as while heated or exposed to heat.

Professional and consumer heating tools can be used as a means to deliver heat or an elevated temperature to the hair. The heating tools can generate heat through electrical current or heating lamps. Depending upon the desired style, these tools include, but are not limited to, heaters, blow dryers, flat irons, hot combs, hot curler sets, heated crimpers, heated lash curlers, heated wands/brushes, and hood driers or their combinations thereof.

In other embodiments, the hair is allowed to air dry after application of the composition, and no heat is applied to the hair. In yet other embodiments, the hair is allowed to air dry after application of the composition, and styled or shaped with no heat being applied to the hair.

As described, compositions according to the disclosure may impart a film on a substrate, such as on the hair or on the hand during or after application to the hair. A film formed by the composition according to certain embodiments may be surprisingly clean-feeling and not sticky, as with traditional hair styling compositions. Also surprisingly, the composition may impart a film on the hair that leaves the hair relatively natural and clean-feeling, yet has a flexible coating, leaving little to no residue, allows the hair to be bouncy and springy with little to no frizz or flaking, may impart relatively high definition with individualized curls, style control, volume, and/or shine, and/or may allow for relatively long-lasting hold and style memory. Furthermore, in at least certain embodiments according to the disclosure, the compositions are not sticky or tacky. A user of hair compositions according to various embodiments described herein may thus feel that the composition is not perceptible or is "invisible," yet still effectively style and/or hold the hair. Additionally, the compositions may have effective hair styling and/or hold properties, even in conditions of high, or relatively high, humidity. In at least certain embodiments according to the disclosure, the compositions may be quick-drying, which may allow drying and/or styling time to be reduced, as well as further improve ease of styling and curl retention.

Furthermore, as described, compositions prepared according to the disclosed embodiments may provide for varying degrees of hold to be imparted to a hair style. By way of non-limiting example only, in order to obtain a spiky look to hair of a very short length, a high level of styling hold may be desirable. Or, as a further non-limiting example, in order to obtain a flowing look or to maintain hair curls for hair of medium length or longer length, a light to medium level of style hold may be desirable. By altering the weight ratio of the first and second polymers, it is possible to formulate compositions having high levels of style hold, medium to high levels of style hold, medium levels of style hold, or light to medium levels of style hold.

In at least certain embodiments, a film formed by the compositions described herein may be clear and/or stable. In such embodiments, phase separation and dramatic aggregation are minimized.

In addition, hair styled or treated with compositions according to the disclosure, in at least certain exemplary embodiments, may be hydrophobic, may appear less frizzy, and/or may be less prone to breakage, relative to hair subjected to the same conditions but not having been styled or treated with a composition according to the disclosure.

It should be noted, however, that compositions and films, as well as hair to which the composition or film has been applied, according to the disclosure may not have one or more of the herein-referenced properties, yet are intended to be within the scope of the disclosure.

Also disclosed herein are methods for styling the hair, said methods comprising applying a composition according to the disclosure to the hair, either before, during, or after styling the hair. One or more steps of treating the hair with an external stimuli, such as heat, before, during, or after the composition has been applied to the hair are also contemplated. Additional methods comprise applying a composition according to disclosure to dry hair to achieve a desired shape.

It is to be understood that both the foregoing description and the following Examples are exemplary and explanatory only, and are not to be interpreted as restrictive of the disclosure. Moreover, it should be understood that various features and/or characteristics of differing embodiments herein may be combined with one another. It is therefore to be understood that numerous modifications may be made to the illustrative embodiments and that other arrangements may be devised without departing from the scope of the disclosure. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a surfactant" is intended to mean at least one surfactant unless the context clearly indicates otherwise.

It should be understood that all patents and published patent applications referenced are incorporated herein in their entireties.

While various features, elements or steps of particular embodiments may be disclosed using the transitional phrase "comprising," it is to be understood that alternative embodiments, including those that may be described using the transitional phrases "consisting" or "consisting essentially of," are implied. Thus, for example, implied alternative embodiments to a method that comprises A+B+C include embodiments where a method consists of A+B+C and embodiments where a method consists essentially of A+B+C. As described, the phrase "at least one of A, B, and C" is intended to include "at least one A or at least one B or at least one C," and is also intended to include "at least one A and at least one B and at least one C."

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on.

All numbers, amounts, ranges, etc., are intended to be modified by the term "about," whether or not so expressly stated. Similarly, a range given of "about 1% to 10%" is intended to have the term "about" modifying both the 1% and the 10% endpoints.

Unless otherwise expressly stated, it is in no way intended that any method set forth herein be construed as requiring that its steps be performed in a specific order. Accordingly, where a method claim does not expressly recite an order to be followed by its steps or it is not otherwise specifically stated in the claims or descriptions that the steps are to be limited to a specific order, it is no way intended that any particular order be inferred.

It should be understood that compositions according to various embodiments of the disclosure form a film when applied to a substrate. However, the various properties of the film described herein are intended to include any film provided by compositions according to the disclosure, regardless of whether the film is attached or bonded to the substrate or not. By way of example only, once the compositions are applied to a substrate and a film is formed, the film may subsequently be removed in order to evaluate properties such as strain and Young's modulus.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. For example, the term "about" can mean within 10% of the indicated number (e.g. "about 10%" means 9%-11% and "about 2%" means 1.8%-2.2%), such as within 9%, 8%, 7%, 6%, 5%, 4%, 3%, 2%, or 1%, according to various embodiments.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

It is understood that when an amount of a component is given, it is intended to signify the amount of the active material, unless otherwise indicated.

The compositions and methods according to the present disclosure can comprise, consist of, or consist essentially of the elements and limitations described herein, as well as any additional or optional ingredients, components, or limitations described herein or otherwise known in the art.

EXAMPLES

The following Examples are intended to be non-restrictive and explanatory only, with the scope of the disclosed embodiments.

The ingredient amounts in the compositions/formulas described below are expressed in % by weight, based on the total weight of the composition.

TABLE 1

| US INCI NAME | Example 1 | Example 2 | Example 3 | Comparative Example 4 | Comparative Example 5 |
|---|---|---|---|---|---|
| Acrylates copolymer | 0.62 | 0.62 | 1.411 | 1.44 | 1.41 |
| Polyurethane-34 | 0.31 | 0.31 | 0.47 | 0.48 | 0.47 |
| Polyacrylate-3 | 0.43 | 0.43 | 0.43 | 0.62 | 0.61 |
| Amodimethicone/ Morpholinomethylsilsesquioxane copolymer | 0.26 | 0.26 | 0.26 | | |
| Amodimethicone | 0.40 | 0.40 | 0.40 | | |
| Caprylyl Methicone | | | | 0.29 | |
| Dimethicone | | | | 0.17 | |
| Dimethiconol | | | | 0.02 | |
| Cocamidopropyl Betaine | 0.07 | 0.07 | 0.07 | 0.07 | |
| Decyl Glucoside | 0.1 | 0.1 | 0.1 | | |
| Hydroxypropyl Guar | 0.09 | 0.09 | 0.09 | | |
| Propylene Glycol | 0.94 | 0.94 | 0.94 | 0.96 | |
| Isopropane (and) Butane | 6.9 | 6.0 | 6.0 | 4.0 | 6.0 |
| Nonionic surfactants (Polysorbate 20, Polysorbate 80, and Trideceth-10) | 0.32 | 0.32 | 0.38 | | |
| Nonionic surfactants (Polysorbate 20, Polysorbate 80) | | | | 0.31 | |
| Nonionic surfactants (Polysorbate 80) | | | | | 0.12 |
| Lauramine Oxide | | | | 0.086 | |
| Additional Components (e.g., surfactants, organic solvents, preservatives, neutralizing agents, salt, and fragrances) | 1.38 | 1.67 | 1.72 | 1.51 | 1.40 |
| Water qs | 100 | 100 | 100 | 100 | 100 |

TABLE 2

| US INCI NAME | Example 6 | Example 7 |
|---|---|---|
| Acrylates copolymer | 0.66 | 1.41 |
| Polyurethane-34 | 0.33 | 0.47 |
| Polyacrylate-3 | 0.46 | 0.43 |
| Trideceth-9 PG Amodimethicone | 0.35 | 0.33 |
| PEG PEG-40/PPG-8 Methylaminopropyl/ hydroxylpropyl dimethicone copolymer | 0.6 | |
| Amodimethicone | | 0.33 |
| Cocamidopropyl Betaine | 0.076 | 0.071 |
| Decyl Glucoside | 0.11 | 0.10 |
| Hydroxypropyl Guar | | 0.094 |
| Isopropane (and) Butane | | 6.0 |
| Nonionic surfactants (Polysorbate 20, Polysorbate 80, and Trideceth-12) | 0.31 | |
| Nonionic surfactants (Polysorbate 20, Polysorbate 80, Trideceth-10, and Trideceth-12) | | 0.40 |
| Additional Components (e.g., surfactants, organic solvents, preservatives, neutralizing agents, salt, and fragrances) | 1.12 | 1.08 |
| Water qs | 100 | 100 |

According to Tables 1 and 2 above, Examples 1, 2, 3, 6 and 7 and Comparative Examples 4 and 5 were prepared based on the following protocol:

A tank contained water. Polyacrylate-3 was added to the tank and the ingredients in the tank were mixed until uniform. Then, a neutralizing agent was added, at which point the batch thickened and turned clear. Surfactants and polymers, including acrylates copolymer and polyurethane-34, were added to the batch. Then, additional surfactants and aminofunctional silicones were added to the batch in Examples 1-3; additional surfactants and non-aminofunctional silicones were added to the batch in Comparative Example 4; and additional surfactants were added to the batch in Comparative Example 5. Solvents, preservatives, and other additional components were added to the batch. The batch was mixed between the additions until it was uniform. Each of the compositions containing propellants (isobutane and propane) was packaged in respective vacuum-sealed pressurized cans; propellants were released through a valve into the vacuum-sealed pressurized cans, wherein the propellants and composition could mix together.

Examples 1-3 and Comparative Examples 4 and 5 were then applied to corresponding locks of wet hair and hair on mannequin heads. A panel of experts evaluated the compositions based on ease of application and distribution on the hair. The panel of experts also evaluated the locks of hair based on hair volume, feel of the hair, and conditioning effects. The treated locks of hair were then blow dried with a round brush, and the panel of experts evaluated the dry treated hair based on the same criteria.

Examples 1, 2, and 3, provided great conditioning properties in both wet and dry stages while maintaining a clean feel and high resistance to humidity. The hair locks treated with Examples 1, 2, and 3 had a clean, natural, and/or "invisible" feel and a lack of stickiness.

In contrast, Comparative Examples 4 and 5 did not provide desirable hair care benefits. Specifically, the hair treated with Comparative Example 4 was heavy and had low volume and a greasy feel. Comparative Example 5 imparted a dry and super clean feel to the hair, which led to difficult application and distribution of the product, dryness, and static in the hair. Further, Comparative Examples 4 and 5 did not provide conditioning effects after the treated hair locks were blow dried.

Both examples 6 and 7 imparted to hair a natural/clean feel (no residue, no flaking, not sticky), a touchable feel, frizz control, long lasting natural shape control and lightweight feel to the hair (did not give a heavy feeling to the hair).

Example 6 provided to the hair more flexible hold and additional shine while providing a hold that resulted in a textured look.

Example 7 provided a strong hold and enhanced the natural waves and curls of the hair.

What is claimed is:

1. A cosmetic composition comprising:
   at least two latex polymers comprising at least one acrylate latex polymer and at least one polyurethane latex polymer; and
   at least one aminofunctional silicone chosen
from amodimethicone/morpholinomethyl silsesquioxane copolymer, amodimethicone, PEG-40/PPG-8 methylaminopropyl/hydroxypropyl dimethicone copolymers, trideceth-9 PG-amodimethicone, or mixtures thereof;
   at least one amphoteric surfactant;
   at least one alkylpolyglucoside;
   at least one anionic thickening agent; and
   water;
   wherein the at least two latex polymers are present in a combined amount ranging from about 0.1% to about 30% by weight, relative to the weight of the composition.

2. The cosmetic composition according to claim 1, wherein the at least two latex polymers are present in a combined amount ranging from about 0.25% to about 20% by weight, relative to the total weight of the composition.

3. The cosmetic composition according to claim 1, wherein the weight ratio of the at least one acrylate latex polymer to the at least one polyurethane latex polymer is greater than 1.

4. The cosmetic composition according to claim 1, wherein the weight ratio of the at least one acrylate latex polymer to the at least one polyurethane latex polymer is greater than 2.

5. The cosmetic composition according to claim 1, wherein the weight ratio of the at least one acrylate latex polymer to the at least one polyurethane latex polymer ranges from greater than 1 to about 5.

6. The cosmetic composition according to claim 1, wherein the at least one aminofunctional silicone is present in an amount ranging from about 0.05% to about 10% by weight, relative to the total weight of the composition.

7. The cosmetic composition according to claim 1, wherein the at least one aminofunctional silicone is present in an amount ranging from about 0.25% to about 3% by weight, relative to the total weight of the composition.

8. The cosmetic composition according to claim 1, wherein the at least one amphoteric surfactant is present in an amount ranging from about 0.01% to about 5% by weight, relative to the total weight of the composition.

9. The cosmetic composition according to claim 1, wherein the at least one amphoteric surfactant is present in an amount ranging from about 0.06% to about 3% by weight, relative to the total weight of the composition.

10. The cosmetic composition according to claim 1, wherein the at least one amphoteric surfactant is chosen from cocamidopropyl betaine, coco-betaine, cocoamphodiacetate and its salts, or mixtures thereof.

11. The cosmetic composition according to claim 1, wherein the at least one alkylpolyglucoside is present in an amount ranging from about 0.01% to about 5% by weight, relative to the total weight of the composition.

12. The cosmetic composition according to claim 1, wherein the at least one alkylpolyglucoside is present in an amount ranging from about 0.08% to about 3% by weight, relative to the total weight of the composition.

13. The cosmetic composition according to claim 1, wherein the at least one alkylpolyglucoside is chosen from decyl glucoside, lauryl glucoside, stearyl glucoside, cocoglucoside, or mixtures thereof.

14. The cosmetic composition according to claim 1, wherein the at least one anionic thickening agent is chosen from anionic acrylates copolymers, anionic polyacrylates, or mixtures thereof.

15. The cosmetic composition according to claim 1, wherein the at least one anionic thickening agent is chosen from copolymers of (meth)acrylic acid, methylacrylate and dimethyl meta-isopropenyl benzyl isocyanate of ethoxylated alcohols.

16. The cosmetic composition according to claim 1, wherein the at least one anionic thickening agent is neutralized with alkaline compounds chosen from sodium hydroxide, potassium hydroxide, lithium hydroxide, calcium hydroxide, magnesium hydroxide, barium hydroxide, strontium hydroxide, manganese hydroxide, zinc hydroxide, ammonia, monoethanolamine, diethanolamine, triethanolamine, N-methylglucamine, aminomethyl propanol, aminomethyl propanediol, ethoxylated amines, PEG-25 cocamine, polyoxyethylene (5) cocamine, polyoxyethylene (25) cocamine, polyoxyethylene (5) octadecylamine, polyoxyethylene (25) octadecylamine, polyoxyethylene (5) tallowamine, polyoxyethylene (I5) oleylamine, polyethylene (5) soyamine, polyoxyethylene (25) soyamine, arginine, lysine or mixtures thereof.

17. The cosmetic composition according to claim 1, wherein the at least one anionic thickening agent is present in an amount ranging from about 0.01% to about 15% by weight, relative to the total weight of the composition.

18. The cosmetic composition according to claim 1, wherein the at least one anionic thickening agent is present in an amount ranging from about 0.3% to about 2% by weight, relative to the total weight of the composition.

19. The cosmetic composition according to claim 1, further comprising an additional thickening agent other than the anionic thickening agent and present in a total amount ranging from about 0.01% to about 15% by weight, relative to the total weight of the composition.

20. The cosmetic composition according to claim 1, further comprising at least one propellant.

21. The cosmetic composition according to claim 1, further comprising at least one coalescing agent and/or plasticizer, present in a total amount ranging from about 0.1% to about 20% by weight, relative to the total weight of the composition.

22. The cosmetic composition according to claim 1, further comprising at least one organic solvent.

23. A cosmetic composition comprising:
   at least one acrylate latex polymer;
   at least one polyurethane latex polymer;
   at least one aminofunctional silicone chosen from amodimethicone/morpholinomethyl silsesquioxane copolymer, amodimethicone, PEG-40/PPG-8 methylaminopropyl/hydroxypropyl dimethicone copolymers, trideceth-9 PG-amodimethicone, or mixtures thereof;
   at least one amphoteric surfactant chosen from cocamidopropyl betaine, coco-betaine, cocoamphodiacetate and its salts, or mixtures thereof;

at least one alkylpolyglucoside chosen from decyl glucoside, lauryl glucoside, stearyl glucoside, coco-glucoside, or mixtures thereof;

at least one anionic thickening agent chosen from copolymers of (meth)acrylic acid, methylacrylate and dimethyl meta-isopropenyl benzyl isocyanate of ethoxylated alcohols; and water;

wherein the weight ratio of the at least one acrylate latex polymer to the at least one polyurethane latex polymer is greater than 1.

24. The cosmetic composition according to claim 23, wherein the at least one aminofunctional silicone comprises amodimethicone/morpholinomethyl silsesquioxane copolymer.

25. The cosmetic composition according to claim 23, wherein the at least one aminofunctional silicone comprises trideceth-9 PG-amodimethicone.

26. A method of styling or shaping hair, the method comprising applying to the hair a composition comprising:

at least two latex polymers comprising at least one acrylate latex polymer and at least one polyurethane latex polymer; and at least one aminofunctional silicone chosen from amodimethicone/morpholinomethyl silsesquioxane copolymer, amodimethicone, PEG-40/PPG-8 methylaminopropyl/hydroxypropyl dimethicone copolymers, trideceth-9 PG-amodimethicone, or mixtures thereof;

at least one amphoteric surfactant;

at least one alkylpolyglucoside;

at least one anionic thickening agent; and water.

27. The method of claim 26, further comprising a step of treating the hair with heat at a temperature ranging from about 25° C. to about 250° C. before, during, or after the application of said composition.

28. The method of claim 26, wherein the hair is not treated with heat during or after applying the composition.

* * * * *